(12) United States Patent
Pannerec et al.

(10) Patent No.: US 10,758,560 B2
(45) Date of Patent: Sep. 1, 2020

(54) METHODS FOR TREATING SARCOPENIA AND FRAILTY

(71) Applicant: NESTEC S.A., Vevey (CH)

(72) Inventors: Alice Pannerec, Lausanne (CH); Jerome Feige, Crissier (CH)

(73) Assignee: Societe des Produits Nestle S.A., Vevey (CH)

( * ) Notice: Subject to any disclaimer, the term of this patent is extended or adjusted under 35 U.S.C. 154(b) by 26 days.

(21) Appl. No.: 15/778,791

(22) PCT Filed: Dec. 8, 2016

(86) PCT No.: PCT/EP2016/080182
§ 371 (c)(1),
(2) Date: May 24, 2018

(87) PCT Pub. No.: WO2017/108419
PCT Pub. Date: Jun. 29, 2017

(65) Prior Publication Data
US 2018/0353534 A1    Dec. 13, 2018

(30) Foreign Application Priority Data

Dec. 22, 2015  (EP) .................................. 15202017
Jul. 25, 2016  (EP) .................................. 16180946

(51) Int. Cl.
| | | |
|---|---|---|
| *A61K 38/16* | (2006.01) | |
| *A61K 38/17* | (2006.01) | |
| *A61K 38/18* | (2006.01) | |
| *A61K 31/714* | (2006.01) | |
| *C07K 14/435* | (2006.01) | |
| *C07K 14/475* | (2006.01) | |
| *G01N 33/50* | (2006.01) | |
| *G01N 33/68* | (2006.01) | |
| *A61P 43/00* | (2006.01) | |

(52) U.S. Cl.
CPC ............ *A61K 31/714* (2013.01); *A61K 38/18* (2013.01); *A61K 38/1883* (2013.01); *G01N 33/5023* (2013.01); *G01N 33/6893* (2013.01); *A61P 43/00* (2018.01); *G01N 2800/10* (2013.01); *G01N 2800/50* (2013.01); *G01N 2800/7042* (2013.01)

(58) Field of Classification Search
None
See application file for complete search history.

(56) References Cited

U.S. PATENT DOCUMENTS

2009/0291893 A1  11/2009 Ford
2013/0079281 A1* 3/2013 Zhou .................. A61K 38/1883
514/9.6

FOREIGN PATENT DOCUMENTS

| WO | 2003099300 A1 | 12/2003 |
|---|---|---|
| WO | 2011011252 A1 | 1/2011 |
| WO | 2011011388 A2 | 1/2011 |
| WO | 2011147981 A2 | 12/2011 |

OTHER PUBLICATIONS

Lynch G S: "Emerging Drugs for Sarcopenia: Age-Related Muscle Wasting", Expert Opinion on Emerging Drugs, Informa Healthcare, UK, vol. 9, No. 2, Jan. 1, 2004 (Jan. 1, 2004), pp. 345-361.
Mahanthappa N et al: "Glial Growth Factor 2, A Soluble Neuregulin, Directly Increases Schwann Cell Motility and Indirectly Promotes Neurite Outgrowth", Journal of Neuroscience, Society for Neuroscience, US, vol. 16, No. 15, Aug. 1, 1996 (Aug. 1, 1996), pp. 4673-4683.
Ali S et al: "Sarcopenia, Cachexia and Aging: Diagnosis, Mechanisms and Therapeutic Options—A Mini-Review", Gerontology, vol. 60, No. 4, Jan. 1, 2014 (Jan. 1, 2014), pp. 294-305.
Mithal A et al: "Impact of nutrition on muscle mass, strength, and performance in older adults", Osteoporosis International, vol. 24, No. 5, Dec. 18, 2012 (Dec. 18, 2012), pp. 1555-1566.
Hughes CF et al: "Vitamin B12 and ageing: current issues and interaction with folate", Annals of Clinical Biochemistry., vol. 50, No. 4, Jul. 1, 2013 (Jul. 1, 2013), pp. 315-329.
Viatcheslav Wlassoff, PhD: "Vitamin B12 Deficiency and its Neurological Consequences", Brainblogger.com Jul. 30, 2014 (Jul. 30, 2014), pp. 1-3.
Brady J: "Age and Exercise Related Changes in Motor Neuron Neuregulin and NT-4; Implications for Sarcopenia", Otago University, Mar. 2015 (Mar. 2015).
Grober U et al: "Neuroenhancement with Vitamin B12—Underestimated Neurological Significance", Nutrients, vol. 5, No. 12, Dec. 12, 2013 (Dec. 12, 2013), pp. 5031-5045.
Santilli V et al: "Clinical definition of sarcopenia", Clinical Cases in Mineral and Bone Metabolism, vol. 11, Jan. 1, 2014 (Jan. 1, 2014), pp. 177-180.
Xue: "The Frailty Syndrome: Definition and Natural History", Clinics in Geriatric Medicine., vol. 27, No. 1, Feb. 1, 2011 (Feb. 1, 2011), pp. 1-15.
Sayer, A.A. et al. (2013) New horizons in the pathogenesis, diagnosis and management of sarcopenia. Age Ageing 42: 145-150.
Morley, J.E. et al. (2013) Frailty consensus: a call to action. J. Am. Med. Dir. Assoc. 14: 392-397.

(Continued)

*Primary Examiner* — Christine J Saoud
*Assistant Examiner* — Jon M Lockard
(74) *Attorney, Agent, or Firm* — K&L Gates LLP

(57) ABSTRACT

Neuregulin-1 (NRG1) or a fragment thereof or vitamin B12 for use in maintaining or increasing muscle function and/or mass in an ageing subject, and/or substantially preventing or reducing muscle wasting in an ageing subject.

6 Claims, 14 Drawing Sheets
Specification includes a Sequence Listing.

(56) References Cited

OTHER PUBLICATIONS

Sambrook, J., Fritsch, E.F. and Maniatis, T. (1989) Molecular Cloning: A Laboratory Manual, 2nd Edition, Cold Spring Harbor Laboratory Press.
Ausubel, F.M. et al. (1995 and periodic supplements) Current Protocols in Molecular Biology, Ch. 9, 13 and 16, John Wiley & Sons.
Roe, B., Crabtree, J. and Kahn, A. (1996) DNA 5 Isolation and Sequencing: Essential Techniques, John Wiley & Sons.
Polak, J.M. and McGee, J.O'D. (1990) In Situ Hybridization: Principles and Practice, Oxford University Press.
Gait, M.J. (1984) Oligonucleotide Synthesis: A Practical Approach, IRL Press.
Lilley, D.M. and Dahlberg, J.E. (1992) Methods in Enzymology: DNA Structures Part A: Synthesis and Physical Analysis of DNA, Academic Press.
Yarden, Y. and Sliwkowski MX. (2001) Untangling the ErbB signalling network. Nat. Rev. Mol. Cell Biol. 2: 127-137.
Gambarotta, G. et al. (2013) Neuregulin 1 role in Schwann cell regulation and potential applications to promote peripheral nerve regeneration. Int. Rev. Neurobiol. 108: 223-256.
Stassart, R.M. et al. (2013) A role for Schwann cell-derived neuregulin-1 in remyelination. Nat. Neurosci. 16: 48-54.
Fricker, F.R. et al. (2011) Axonally derived neuregulin-1 is required for remyelination and regeneration after nerve injury in adulthood. J. Neurosci. 31: 3225-3233.
National Academy of Sciences, Institute of Medicine (2000); Dietary Reference Intakes for Thiamin, Riboflavin, Niacin, Vitamin B6, Folate, Vitamin B12, Pantothenic Acid, Biotin and Choline, Chapter 9, pp. 306-356, Washington (DC): National Academies Press (US); 1998.
Le Blanc et al. (2011) B-group vitamin production by lactic acid bacteria—current knowledge and potential applications. J Appl Microbiol. Dec. 2011;111(6):1297-309.
Devereux et al. (1984) A comprehensive set of sequence analysis programs for the VAX. Nucleic Acids Res. 12: 387.
Ausubel et al. (1999) Short Protocols in Molecular Biology : A Compendium of Methods from Current Protocols in Molecular Biology—Ch. 18, and pp. 758-760. John Wiley & Sons, ISBN: 047132938X, 4th edition (Apr. 1999).
Atschul et al. (1990) Basic local alignment search tool. J. Mol. Biol. 403-410.
Tatusova TA and Madden TL, BLAST 2 Sequences, a new tool for comparing protein and nucleotide sequences. FEMS Microbiol. Lett. (1999) 174: 247-50.
Gold, L. et al. (2010) Aptamer-based multiplexed proteomic technology for biomarker discovery. PLoS ONE 5: e15004.
International Search Report for PCT/EP2016/080182.
International Written Opinion for PCT/EP2016/080182.

\* cited by examiner old CTL vs adult

| GSEA Hallmark cluster name | size | FDR q-value |
|---|---|---|
| Up-regulated | | |
| TNFA SIGNALING VIA NFKB | 161 | $<10^{-4}$ |
| APOPTOSIS | 138 | $<10^{-4}$ |
| P53 PATHWAY | 154 | $<10^{-4}$ |
| EPITHELIAL MESENCHYMAL TRANSITION | 160 | $<10^{-4}$ |
| INFLAMMATORY RESPONSE | 137 | $<10^{-4}$ |
| Down-regulated | | |
| OXIDATIVE PHOSPHORYLATION | 125 | $<10^{-4}$ |
| ADIPOGENESIS | 157 | 0.11551 | old AdoCbl vs old CTL

| GSEA Hallmark cluster name | size | FDR q-value |
|---|---|---|
| Up-regulated | | |
| MYC TARGETS | 137 | $<10^{-4}$ |
| OXIDATIVE PHOSPHORYLATION | 117 | $<10^{-4}$ |
| PROTEIN SECRETION | 75 | 0.00017 |
| DNA REPAIR | 102 | 0.00023 |
| ADIPOGENESIS | 155 | 0.00285 |
| Down-regulated | | |
| INFLAMMATORY RESPONSE | 142 | 0.01980 |
| KRAS SIGNALING | 128 | 0.02904 | old MeCbl vs old CTL

| GSEA Hallmark cluster name | size | FDR q-value |
|---|---|---|
| Up-regulated | | |
| MYC TARGETS | 137 | $<10^{-4}$ |
| MYOGENESIS | 161 | 0.02591 |
| PROTEIN SECRETION | 75 | 0.03626 |
| DNA REPAIR | 102 | 0.04126 |
| MTORC1 SIGNALING | 155 | 0.05291 |
| Down-regulated | | |
| INTERFERON ALPHA RESPONSE | 83 | 0.00765 |
| INTERFERON GAMMA RESPONSE | 154 | 0.09843 |

SEQUENCE LISTING

```
<160> NUMBER OF SEQ ID NOS: 8

<210> SEQ ID NO 1
<211> LENGTH: 167
<212> TYPE: PRT
<213> ORGANISM: Homo sapiens

<400> SEQUENCE: 1

Met Ser Glu Arg Lys Glu Gly Arg Gly Lys Gly Lys Gly Lys Lys Lys
1               5                   10                  15
```

-continued

Glu Arg Gly Ser Gly Lys Lys Pro Glu Ser Ala Ala Gly Ser Gln Ser
                20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
            115                 120                 125

Ile Val Glu Ser Asn Glu Ile Ile Thr Gly Met Pro Ala Ser Thr Glu
        130                 135                 140

Gly Ala Tyr Val Ser Ser Glu Ser Pro Ile Arg Ile Ser Val Ser Thr
145                 150                 155                 160

Glu Gly Ala Asn Thr Ser Ser
                165

<210> SEQ ID NO 2
<211> LENGTH: 645
<212> TYPE: PRT
<213> ORGANISM: Homo sapiens

<400> SEQUENCE: 2

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
                20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
            115                 120                 125

Ile Val Glu Ser Asn Glu Ile Ile Thr Gly Met Pro Ala Ser Thr Glu
        130                 135                 140

Gly Ala Tyr Val Ser Ser Glu Ser Pro Ile Arg Ile Ser Val Ser Thr
145                 150                 155                 160

Glu Gly Ala Asn Thr Ser Ser Thr Ser Thr Ser Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
            195                 200                 205

Leu Cys Lys Cys Pro Asn Glu Phe Thr Gly Asp Arg Cys Gln Asn Tyr

-continued

```
            210                 215                 220
Val Met Ala Ser Phe Tyr Lys His Leu Gly Ile Glu Phe Met Glu Ala
225                 230                 235                 240

Glu Glu Leu Tyr Gln Lys Arg Val Leu Thr Ile Thr Gly Ile Cys Ile
                245                 250                 255

Ala Leu Leu Val Val Gly Ile Met Cys Val Val Ala Tyr Cys Lys Thr
                260                 265                 270

Lys Lys Gln Arg Lys Lys Leu His Asp Arg Leu Arg Gln Ser Leu Arg
                275                 280                 285

Ser Glu Arg Asn Asn Thr Met Asn Ile Ala Asn Gly Pro His His Pro
    290                 295                 300

Asn Pro Pro Glu Asn Val Gln Leu Val Asn Gln Tyr Val Ser Lys
305                 310                 315                 320

Asn Val Ile Ser Ser Glu His Ile Val Glu Arg Glu Ala Glu Thr Ser
                325                 330                 335

Phe Ser Thr Ser His Tyr Thr Ser Thr Ala His His Ser Thr Thr Val
                340                 345                 350

Thr Gln Thr Pro Ser His Ser Trp Ser Asn Gly His Thr Glu Ser Ile
                355                 360                 365

Leu Ser Glu Ser His Ser Val Ile Val Met Ser Ser Val Glu Asn Ser
370                 375                 380

Arg His Ser Ser Pro Thr Gly Pro Arg Gly Arg Leu Asn Gly Thr
385                 390                 395                 400

Gly Gly Pro Arg Glu Cys Asn Ser Phe Leu Arg His Ala Arg Glu Thr
                405                 410                 415

Pro Asp Ser Tyr Arg Asp Ser Pro His Ser Glu Arg Tyr Val Ser Ala
                420                 425                 430

Met Thr Thr Pro Ala Arg Met Ser Pro Val Asp Phe His Thr Pro Ser
                435                 440                 445

Ser Pro Lys Ser Pro Pro Ser Glu Met Ser Pro Pro Val Ser Ser Met
    450                 455                 460

Thr Val Ser Met Pro Ser Met Ala Val Ser Pro Phe Met Glu Glu Glu
465                 470                 475                 480

Arg Pro Leu Leu Leu Val Thr Pro Pro Arg Leu Arg Glu Lys Lys Phe
                485                 490                 495

Asp His His Pro Gln Gln Phe Ser Ser Phe His His Asn Pro Ala His
                500                 505                 510

Asp Ser Asn Ser Leu Pro Ala Ser Pro Leu Arg Ile Val Glu Asp Glu
                515                 520                 525

Glu Tyr Glu Thr Thr Gln Glu Tyr Glu Pro Ala Gln Glu Pro Val Lys
    530                 535                 540

Lys Leu Ala Asn Ser Arg Arg Ala Lys Arg Thr Lys Pro Asn Gly His
545                 550                 555                 560

Ile Ala Asn Arg Leu Glu Val Asp Ser Asn Thr Ser Ser Gln Ser Ser
                565                 570                 575

Asn Ser Glu Ser Glu Thr Glu Asp Glu Arg Val Gly Glu Asp Thr Pro
                580                 585                 590

Phe Leu Gly Ile Gln Asn Pro Leu Ala Ala Ser Leu Glu Ala Thr Pro
                595                 600                 605

Ala Phe Arg Leu Ala Asp Ser Arg Thr Asn Pro Ala Gly Arg Phe Ser
                610                 615                 620

Thr Gln Glu Glu Ile Gln Ala Arg Leu Ser Ser Val Ile Ala Asn Gln
625                 630                 635                 640
```

Asp Pro Ile Ala Val
            645

<210> SEQ ID NO 3
<211> LENGTH: 637
<212> TYPE: PRT
<213> ORGANISM: Homo sapiens

<400> SEQUENCE: 3

Met Ser Glu Arg Lys Glu Gly Arg Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
        195                 200                 205

Leu Cys Lys Cys Pro Asn Glu Phe Thr Gly Asp Arg Cys Gln Asn Tyr
    210                 215                 220

Val Met Ala Ser Phe Tyr Lys Ala Glu Glu Leu Tyr Gln Lys Arg Val
225                 230                 235                 240

Leu Thr Ile Thr Gly Ile Cys Ile Ala Leu Leu Val Val Gly Ile Met
                245                 250                 255

Cys Val Val Ala Tyr Cys Lys Thr Lys Lys Gln Arg Lys Lys Leu His
            260                 265                 270

Asp Arg Leu Arg Gln Ser Leu Arg Ser Glu Arg Asn Asn Thr Met Asn
        275                 280                 285

Ile Ala Asn Gly Pro His His Pro Asn Pro Pro Pro Glu Asn Val Gln
    290                 295                 300

Leu Val Asn Gln Tyr Val Ser Lys Asn Val Ile Ser Ser Glu His Ile
305                 310                 315                 320

Val Glu Arg Glu Ala Glu Thr Ser Phe Ser Thr Ser His Tyr Thr Ser
                325                 330                 335

Thr Ala His His Ser Thr Thr Val Thr Gln Thr Pro Ser His Ser Trp
            340                 345                 350

Ser Asn Gly His Thr Glu Ser Ile Leu Ser Glu Ser His Ser Val Ile

```
                355                 360                 365
Val Met Ser Ser Val Glu Asn Ser Arg His Ser Pro Thr Gly Gly
    370                 375                 380

Pro Arg Gly Arg Leu Asn Gly Thr Gly Gly Pro Arg Glu Cys Asn Ser
385                 390                 395                 400

Phe Leu Arg His Ala Arg Glu Thr Pro Asp Ser Tyr Arg Asp Ser Pro
                405                 410                 415

His Ser Glu Arg Tyr Val Ser Ala Met Thr Thr Pro Ala Arg Met Ser
            420                 425                 430

Pro Val Asp Phe His Thr Pro Ser Ser Pro Lys Ser Pro Pro Ser Glu
        435                 440                 445

Met Ser Pro Pro Val Ser Ser Met Thr Val Ser Met Pro Ser Met Ala
    450                 455                 460

Val Ser Pro Phe Met Glu Glu Arg Pro Leu Leu Leu Val Thr Pro
465                 470                 475                 480

Pro Arg Leu Arg Glu Lys Lys Phe Asp His His Pro Gln Gln Phe Ser
                485                 490                 495

Ser Phe His His Asn Pro Ala His Asp Ser Asn Ser Leu Pro Ala Ser
            500                 505                 510

Pro Leu Arg Ile Val Glu Asp Glu Glu Tyr Glu Thr Thr Gln Glu Tyr
        515                 520                 525

Glu Pro Ala Gln Glu Pro Val Lys Lys Leu Ala Asn Ser Arg Arg Ala
    530                 535                 540

Lys Arg Thr Lys Pro Asn Gly His Ile Ala Asn Arg Leu Glu Val Asp
545                 550                 555                 560

Ser Asn Thr Ser Ser Gln Ser Ser Asn Ser Glu Ser Glu Thr Glu Asp
                565                 570                 575

Glu Arg Val Gly Glu Asp Thr Pro Phe Leu Gly Ile Gln Asn Pro Leu
            580                 585                 590

Ala Ala Ser Leu Glu Ala Thr Pro Ala Phe Arg Leu Ala Asp Ser Arg
        595                 600                 605

Thr Asn Pro Ala Gly Arg Phe Ser Thr Gln Glu Glu Ile Gln Ala Arg
    610                 615                 620

Leu Ser Ser Val Ile Ala Asn Gln Asp Pro Ile Ala Val
625                 630                 635

<210> SEQ ID NO 4
<211> LENGTH: 241
<212> TYPE: PRT
<213> ORGANISM: Homo sapiens

<400> SEQUENCE: 4

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
                20                  25                  30

Pro Ala Leu Pro Pro Arg Leu Lys Glu Met Lys Ser Gln Glu Ser Ala
            35                  40                  45

Ala Gly Ser Lys Leu Val Leu Arg Cys Glu Thr Ser Ser Glu Tyr Ser
        50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95
```

Leu Arg Ile Asn Lys Ala Ser Leu Ala Asp Ser Gly Glu Tyr Met Cys
                100                 105                 110

Lys Val Ile Ser Lys Leu Gly Asn Asp Ser Ala Ser Ala Asn Ile Thr
            115                 120                 125

Ile Val Glu Ser Asn Glu Ile Ile Thr Gly Met Pro Ala Ser Thr Glu
        130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Thr Gly Thr
                165                 170                 175

Ser His Leu Val Lys Cys Ala Glu Lys Glu Lys Thr Phe Cys Val Asn
                180                 185                 190

Gly Gly Glu Cys Phe Met Val Lys Asp Leu Ser Asn Pro Ser Arg Tyr
            195                 200                 205

Leu Cys Lys Cys Pro Asn Glu Phe Thr Gly Asp Arg Cys Gln Asn Tyr
        210                 215                 220

Val Met Ala Ser Phe Tyr Ser Thr Ser Thr Pro Phe Leu Ser Leu Pro
225                 230                 235                 240

Glu

<210> SEQ ID NO 5
<211> LENGTH: 211
<212> TYPE: PRT
<213> ORGANISM: Homo sapiens

<400> SEQUENCE: 5

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
                100                 105                 110

Lys Val Ile Ser Lys Leu Gly Asn Asp Ser Ala Ser Ala Asn Ile Thr
            115                 120                 125

Ile Val Glu Ser Asn Glu Ile Ile Thr Gly Met Pro Ala Ser Thr Glu
        130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Thr Gly Thr
                165                 170                 175

Ser His Leu Val Lys Cys Ala Glu Lys Glu Lys Thr Phe Cys Val Asn
                180                 185                 190

Gly Gly Glu Cys Phe Met Val Lys Asp Leu Ser Asn Pro Ser Arg Tyr
            195                 200                 205

Leu Cys Lys
        210

<210> SEQ ID NO 6
<211> LENGTH: 300
<212> TYPE: PRT
<213> ORGANISM: Homo sapiens

<400> SEQUENCE: 6

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
        195                 200                 205

Leu Cys Lys Cys Pro Asn Glu Phe Thr Gly Asp Arg Cys Gln Asn Tyr
    210                 215                 220

Val Met Ala Ser Phe Tyr Lys His Leu Gly Ile Glu Phe Met Glu Gln
225                 230                 235                 240

Lys Arg Val Leu Thr Ile Thr Gly Ile Cys Ile Ala Leu Leu Val Val
                245                 250                 255

Gly Ile Met Cys Val Val Ala Tyr Cys Lys Thr Lys Lys Gln Arg Lys
            260                 265                 270

Lys Leu His Asp Arg Leu Arg Gln Ser Leu Arg Ser Glu Arg Asn Asn
        275                 280                 285

Met Met Asn Ile Ala Asn Gly Pro His His Pro Asn
    290                 295                 300

<210> SEQ ID NO 7
<211> LENGTH: 61
<212> TYPE: PRT
<213> ORGANISM: Homo sapiens

<400> SEQUENCE: 7

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

```
Leu Cys Lys Cys Pro Asn Glu Phe Thr Gly Asp Arg Cys Gln Asn Tyr
        35                  40                  45

Val Met Ala Ser Phe Tyr Lys His Leu Gly Ile Glu Phe
    50                  55                  60

<210> SEQ ID NO 8
<211> LENGTH: 44
<212> TYPE: PRT
<213> ORGANISM: Homo sapiens

<400> SEQUENCE: 8

His Leu Val Lys Cys Ala Glu Lys Glu Lys Thr Phe Cys Val Asn Gly
1               5                   10                  15

Gly Glu Cys Phe Met Val Lys Asp Leu Ser Asn Pro Ser Arg Tyr Leu
            20                  25                  30

Cys Lys Cys Gln Pro Gly Phe Thr Gly Ala Arg Cys
        35                  40
```

METHODS FOR TREATING SARCOPENIA AND FRAILTY

CROSS-REFERENCES TO RELATED APPLICATIONS

The present application is the National Stage of International Application No. PCT/EP2016/080182, filed on Dec. 8, 2016, which claims benefit to European Application No. 15202017.8, filed Dec. 22, 2015, and European Application No. 16180946.2, filed Jul. 25, 2016. The entire contents of the above applications are incorporated by reference as if recited in full herein.

FIELD OF THE INVENTION

The present invention relates to the use of neuregulin-1 (NRG1) and/or vitamin B12 for maintaining or increasing muscle function and/or muscle mass in ageing subjects. In particular, the invention relates to the use of NRG1 and/or vitamin B12 for treating sarcopenia or physical frailty.

BACKGROUND TO THE INVENTION

Age-related loss of muscle function and mass occurs inevitably in all individuals, however its progression depends on a range of genetic and environmental factors, such as physical activity and nutritional intake.

In some subjects, the effect of ageing on muscle may progress to a state of morbidity, specific conditions of which include sarcopenia and frailty. Sarcopenia is defined as occurring at the point at which the age-related loss of muscle function and mass becomes debilitating and impacts on quality of life (Sayer, A. A. et al. (2013) Age Ageing 42: 145-150). In contrast, frailty is a classification of age-related muscle dysfunction which relies on muscle strength and functionality, but not muscle mass (Morley, J. E. et al. (2013) J. Am. Med. Dir. Assoc. 14: 392-397).

Sarcopenia and frailty are multi-factorial syndromes which associate with pathophysiological changes, such as impaired neuro-muscular transition, altered excitation/contraction coupling, impaired regenerative capacity linked to stem cell exhaustion, defects of mitochondrial and energy metabolism in myofibers, and marbling of skeletal muscle with fat and fibrosis (Ali, S. et al. (2014) Gerontology 60: 294-305). The aetiology of these syndromes is therefore complex and poorly understood, but low physical activity, hormonal decline in anabolic hormones (e.g. androgens and IGF-1), and malnutrition and/or nutritional deficiencies play an important role (Mithal, A. et al. (2013) Osteoporos. Int. 24: 1555-1566).

Sarcopenia is becoming a major health concern in developed countries, where lessened physical activity with age and increased longevity are particularly prevalent. In severe cases, sarcopenia may result in a person losing their ability to live independently. In addition, sarcopenia is a predictor of wider-ranging disability in population-based studies, and has been linked to poor balance, gait speed, prevalence of falls and fractures.

Reduced physical activity is thought to increase the likelihood of sarcopenia and therefore increased exercise will likely be beneficial in combating the condition. Indeed, resistance exercise is associated with increased synthesis of proteins in skeletal muscle. However, exercise as a treatment often suffers from poor patient compliance.

There are currently no pharmacological agents approved for the treatment of sarcopenia. A number of growth hormones have been studied in this context, however these have shown little effect. In addition, anabolic steroids may increase muscle mass and strength, but are associated with a number of side effects, such as increased risk of prostate cancer. Moreover, existing pharmacological and nutritional approaches are mainly directed at targeting muscle anabolism and do not adequately address the neuromuscular defects associated with the condition.

Accordingly there remains a significant need for methods of maintaining or increasing muscle function and mass in ageing subjects. In particular, there is a need for methods of treating sarcopenia and frailty.

SUMMARY OF THE INVENTION

The role of neuregulin-1 (NRG1) in both nerve and muscle development and maintenance has been studied for some time. For example, NRG1 is known to be produced by muscle and to be essential for myogenic differentiation. It has also been shown that NRG1 is involved in signalling cascades for contraction and glucose metabolism. However, no link has been previously made between NRG1 levels and the age of an individual.

The present inventors have surprisingly found that expression of NRG1 decreases with age. Having established the link between age and NRG1, the inventors proceeded to demonstrate that increasing NRG1 levels in ageing animal models reversed the wasting effect of age on muscle.

In summary, the inventors have unexpectedly found that increasing levels of NRG1 in ageing subjects is clinically applicable to the treatment of age-related decline in muscle function and mass, and therefore provides a route to the treatment of age-related conditions such as sarcopenia and frailty.

In addition, the inventors have unexpectedly found that increasing levels of vitamin B12 in ageing subjects is clinically applicable to the treatment of age-related decline in muscle function and mass, and therefore provides a route to the treatment of age-related conditions such as sarcopenia and frailty.

In particular, the inventors have surprisingly found that different vitamin B12 isoforms have particular effects on different systems and pathways. Accordingly, particular vitamin B12 isoforms, or combinations of vitamin B12 isoforms, can be chosen to provide particularly beneficial effects in a subject.

Accordingly, in one aspect, the invention provides neuregulin-1 (NRG1) or a fragment thereof for use in maintaining or increasing muscle function and/or mass in an ageing subject, and/or substantially preventing or reducing muscle wasting in an ageing subject.

In another aspect, the invention provides vitamin B12 for use in maintaining or increasing muscle function and/or mass in an ageing subject, and/or substantially preventing or reducing muscle wasting in an ageing subject.

The ageing subject may, for example, be a human subject over the age of 30, 35, 40, 45, 50, 55, 60, 65, 70, 75, 80, 85, 90, 95 or 100 years old.

Preferably, the muscle is skeletal muscle.

In one embodiment, the NRG1 or fragment thereof or the vitamin B12 maintains or increases muscle mass.

In another embodiment, the NRG1 or fragment thereof substantially prevents or reduces a reduction in muscle mass. The prevention or reduction in muscle mass may be in comparison to the reduction in muscle mass that would be expected in the absence of the NRG1 or fragment thereof of the invention.

In another embodiment, the vitamin B12 substantially prevents or reduces a reduction in muscle mass. The prevention or reduction in muscle mass may be in comparison to the reduction in muscle mass that would be expected in the absence of the vitamin B12 of the invention.

In another aspect, the invention provides neuregulin-1 (NRG1) or a fragment thereof or vitamin B12 for use in treating sarcopenia or frailty.

The NRG1 or fragment thereof for use according to the invention may be in a combined preparation with vitamin B12 for simultaneous, combined, sequential or separate administration to a subject.

In one embodiment, the NRG1 or fragment thereof of the invention is a NRG1 type I, II, III, IV, V or VI isoform.

Preferably, the NRG1 or fragment thereof of the invention is a NRG1 type I isoform.

In another embodiment, the NRG1 or fragment thereof of the invention is a NRG1 HRG-alpha, HRG-beta or HRG-gamma isoform Preferably, the NRG1 or fragment thereof of the invention is a NRG1 HRG-beta isoform.

In one embodiment, the NRG1 or fragment thereof of the invention is a NRG1 HRG-beta1 isoform. In another embodiment, the NRG1 or fragment thereof of the invention is a NRG1 HRG-beta2 isoform. In another embodiment, the NRG1 or fragment thereof of the invention is a NRG1 HRG-beta3 isoform.

In one embodiment, the NRG1 fragment of the invention comprises an NRG1 EGF domain.

In one embodiment, the NRG1 or fragment thereof of the invention comprises an amino acid sequence selected from the group consisting of:
  (a) an amino acid sequence that has at least 60% identity to SEQ ID NO: 1 or 5;
  (b) an amino acid sequence that has at least 60% identity to SEQ ID NO: 2, 3, 4 or 6; and
  (c) an amino acid sequence that has at least 60% identity to SEQ ID NO: 7 or 8, preferably SEQ ID NO: 7;

Preferably, the NRG1 or fragment thereof provides for maintaining or increasing muscle function and/or mass in an ageing subject and/or substantially preventing or reducing muscle wasting in an ageing subject. Preferably, the NRG1 or fragment thereof substantially retains the natural function of the protein represented by SEQ ID NO: 7.

In another embodiment, the NRG1 or fragment thereof of the invention comprises an amino acid sequence that has at least 60%, 70%, 80%, 90%, 95%, 96%, 97%, 98%, 99% or 100% identity to SEQ ID NO: 1 or 5. Preferably, the NRG1 or fragment thereof provides for maintaining or increasing muscle function and/or mass in an ageing subject and/or substantially preventing or reducing muscle wasting in an ageing subject. Preferably, the NRG1 or fragment thereof substantially retains the natural function of the protein represented by SEQ ID NO: 7.

In another embodiment, the NRG1 or fragment thereof of the invention comprises an amino acid sequence that has at least 60%, 70%, 80%, 90%, 95%, 96%, 97%, 98%, 99% or 100% identity to SEQ ID NO: 2, 3, 4 or 6. Preferably, the NRG1 or fragment thereof provides for maintaining or increasing muscle function and/or mass in an ageing subject and/or substantially preventing or reducing muscle wasting in an ageing subject. Preferably, the NRG1 or fragment thereof substantially retains the natural function of the protein represented by SEQ ID NO: 7.

In another embodiment, the NRG1 or fragment thereof of the invention comprises an amino acid sequence that has at least 60%, 70%, 80%, 90%, 95%, 96%, 97%, 98%, 99% or 100% identity to SEQ ID NO: 7 or 8, preferably SEQ ID NO: 7. Preferably, the NRG1 or fragment thereof provides for maintaining or increasing muscle function and/or mass in an ageing subject and/or substantially preventing or reducing muscle wasting in an ageing subject. Preferably, the NRG1 or fragment thereof substantially retains the natural function of the protein represented by SEQ ID NO: 7.

Preferably, the NRG1 or fragment thereof of the invention provides a similar or increased effect of:
  (a) maintaining or increasing muscle function and/or mass in an ageing subject;
  (b) preventing or reducing muscle wasting in an ageing subject; and/or
  (c) treating sarcopenia or frailty,
  compared to the protein of SEQ ID NO: 7.

In another aspect, the invention provides a polypeptide comprising a NRG1 EGF domain for use in maintaining or increasing muscle function and/or mass in an ageing subject, and/or substantially preventing or reducing muscle wasting in an ageing subject.

In one embodiment, the NRG1 or fragment thereof maintains or increases muscle mass.

In another aspect, the invention provides a polypeptide comprising a NRG1 EGF domain for use in treating sarcopenia or frailty.

The use may be as described herein.

In one embodiment, the vitamin B12 may be adenosylcobalamin and/or methylcobalamin.

In another embodiment, the vitamin B12 may be hydroxocobalamin and/or cyanocobalamin which can be converted into methylcobalamin and/or adenosylcobalamin.

In one aspect the present invention provides adenosylcobalamin for use in maintaining or increasing muscle function and/or muscle mass in an ageing subject. In a particular embodiment the present invention provides adenosylcobalamin for use in increasing muscle fiber size in an ageing subject.

In one aspect the present invention provides methylcobalamin for use in substantially preventing or reducing muscle wasting in an ageing subject. In a particular embodiment, the present invention provides methylcobalamin for use in substantially preventing or reducing muscle atrophy in an ageing subject.

In one embodiment the present invention provides a combination of adenosylcobalamin and methylcobalamin for use maintaining or increasing muscle function and/or mass and reducing muscle atrophy in an ageing subject. In a particular embodiment the present invention provides a combination of adenosylcobalamin and methylcobalamin for use increasing muscle fiber size and substantially preventing or reducing muscle atrophy in an ageing subject.

The vitamin B12 may be administered by oral, parental, sub-lingual, sub-cutaneous, transdermal or intra-nasal administration.

The vitamin B12 may be administered as an oral vitamin B12 supplement or a probiotic supplement comprising vitamin B12 producing bacteria. The vitamin B12 may, for example, be in the form of a nutritional composition or supplement, or a diet product.

In one embodiment, the subject may have previously been determined to be vitamin B12 deficient.

In another aspect, the invention provides a method of maintaining or increasing muscle function and/or mass in an ageing subject comprising administering the neuregulin-1 (NRG1) or a fragment thereof or vitamin B12 of the invention to a subject in need thereof.

In one embodiment, the NRG1 or fragment thereof or vitamin B12 or vitamin B12 maintains or increases muscle mass.

In another embodiment, the NRG1 or fragment thereof or vitamin B12 substantially prevents or reduces a reduction in muscle mass.

In another aspect, the invention provides a method of substantially preventing or reducing muscle wasting in an ageing subject comprising administering the neuregulin-1 (NRG1) or a fragment thereof or vitamin B12 of the invention to a subject in need thereof.

The vitamin B12 may maintain or increase muscle function and/or mass, and/or substantially prevent or reduce muscle wasting in a manner as described herein.

In another aspect, the invention provides a method of treating sarcopenia or frailty comprising administering neuregulin-1 (NRG1) or a fragment thereof or vitamin B12 of the invention to a subject in need thereof.

Preferably, the muscle is skeletal muscle.

In another aspect, the invention provides use of the neuregulin-1 (NRG1) or a fragment thereof or vitamin B12 of the invention for the manufacture of a medicament for:
(a) maintaining or increasing muscle function and/or mass in an ageing subject;
(b) substantially preventing or reducing muscle wasting in an ageing subject; and/or
(c) treating sarcopenia or frailty.

In one embodiment, the medicament maintains or increases muscle mass.

In another embodiment, the medicament substantially prevents or reduces a reduction in muscle mass.

In another aspect, the invention provides a combined preparation of neuregulin-1 (NRG1) or a fragment thereof of the invention and vitamin B12, wherein the NRG1 or fragment thereof and vitamin B12 are for simultaneous, combined, sequential or separate administration to a subject.

The vitamin B12 of the combined preparation may, for example, be in the form of a nutritional composition or supplement, or a diet product. The NRG1 of fragments thereof may, for example, be in a form suitable for parenteral administration (e.g. sub-cutaneous, intravenous or intramuscular injection)

In another aspect, the invention provides a method of screening for an agent capable of increasing neuregulin-1 (NRG1) levels in a subject comprising the steps:
(a) contacting a population of cells with a candidate agent;
(b) determining the level of NRG1 in the population of cells; and
(c) comparing the level of NRG1 determined in step (b) with a NRG1 level in a control population of cells which has not been contacted with the candidate agent.

The candidate agent may, for example, be a pharmaceutical agent or nutritional supplement. Preferably, the candidate agent is a nutritional supplement.

In one embodiment, the candidate agent is comprised in a library of candidate agents.

In another aspect, the invention provides an agent for increasing neuregulin-1 (NRG1) levels in a subject, preferably wherein the agent has been identified by the method of screening of the invention.

Preferably, the agent is a nutritional supplement.

The agent may be in a combined preparation with vitamin B12, wherein the agent and vitamin B12 are for simultaneous, combined, sequential or separate administration to a subject.

In another aspect, the invention provides the agent of the invention for use in:
(a) maintaining or increasing muscle function and/or mass in an ageing subject;
(b) substantially preventing or reducing muscle wasting in an ageing subject; and/or
(c) treating sarcopenia or frailty.

Preferably, the muscle is skeletal muscle.

In another aspect, the invention provides a method of diagnosing sarcopenia or frailty comprising the steps:
(a) providing a biological sample isolated from a subject;
(b) determining the level of neuregulin-1 (NRG1) in the biological sample; and
(c) comparing the level of NRG1 determined in step (b) with a NRG1 level determined from one or more control samples or reference levels.

In another aspect, the invention provides a diet product for use in maintaining or increasing muscle function and/or mass in an ageing subject, and/or substantially preventing or reducing muscle wasting in an ageing subject.

In another aspect, the invention provides a diet product for use in treating sarcopenia or frailty.

Preferably, the diet product of the invention is for use in a subject that has been diagnosed as having sarcopenia or frailty, or being at risk of developing sarcopenia or frailty using a method of the invention.

In one embodiment, the diet product of the invention is for use in a vitamin B12 deficient subject.

In another aspect, the neuregulin-1 (NRG1) or fragment thereof; vitamin B12; agent; or diet product of the invention may be used in combination with an exercise regime to maintain or increase muscle function and/or mass.

In another aspect, the neuregulin-1 (NRG1) or fragment thereof; vitamin B12; agent; or diet product of the invention may be used in combination with other pharmaceutical compositions, including selective androgen receptor modulators (SARMs), such as ostarine or myostatin blockers (e.g. myostatin antibodies, activin receptor antibodies and activin receptor-Fc), such as LY2495655 or Bimagrumab, or beta2 receptor agonists such as formoterol, or ghrelin receptor agonists such as anamorelin, or anabolic catabolic transforming agents (ACTA), such as MT-102.

Figure 1:
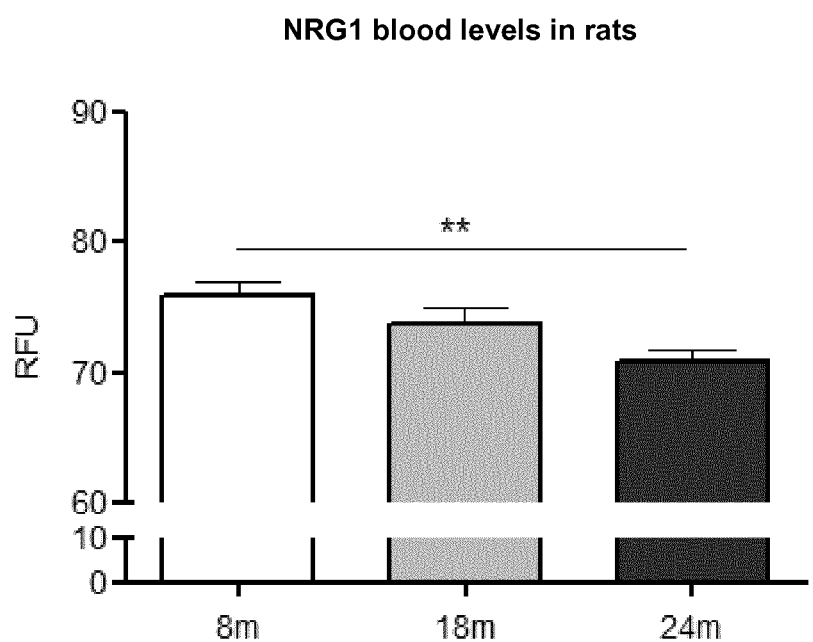
FIG. 1

Circulating Levels of Neuregulin-1 (NRG1) Decrease with Age in Rats.

Neuregulin-1 (NRG1) levels were measured in serum from rats aged 8 months, 18 months or 24 months using the slow off-rate DNA aptamer detection and quantification was performed after median-normalisation of Relative Fluorescence Units (RFU). 10 animals per group were analysed. **=p-value<0.01.

FIG. 2

Neuregulin-1 (NRG1) Protects Neuromuscular Junctions from Damage In Vitro.

Nerve and muscle co-cultures were grown in vitro until neuromuscular junctions were mature. Damage was induced using beta-amyloid (Ab) incubation (2.5 μM) and riluzole was used as a positive control for preserving neuromuscular junctions from Ab-induced damage. The effect of neuregulin-1 (NRG1) on Ab-induced damage was evaluated by measuring the neuromuscular junction (NMJ) size. All values are from 6 wells per group and are shown as a percent of the control condition (CTL). =p-value<0.01; *=p-value<0.001.

FIG. 3

Neuregulin-1 (NRG1) Protects Skeletal Muscle from Age-Induced Atrophy.

Pre-sarcopenic rats aged 16 months were treated for 5 months with either neuregulin-1 (NRG1) or saline. NRG1 was injected sub-cutaneously at 1 μg/kg body weight 3 times per week. Hind-limb skeletal muscle mass was then evaluated and compared to a group of adult healthy rats (8 months old at the start of the experiment) injected with saline control. *=p-value<0.05; **=p-value<0.01.

FIGS. 4A-C

Vitamin B12 Protects Neuromuscular Junctions from Damage In Vitro.

Figure 4A:
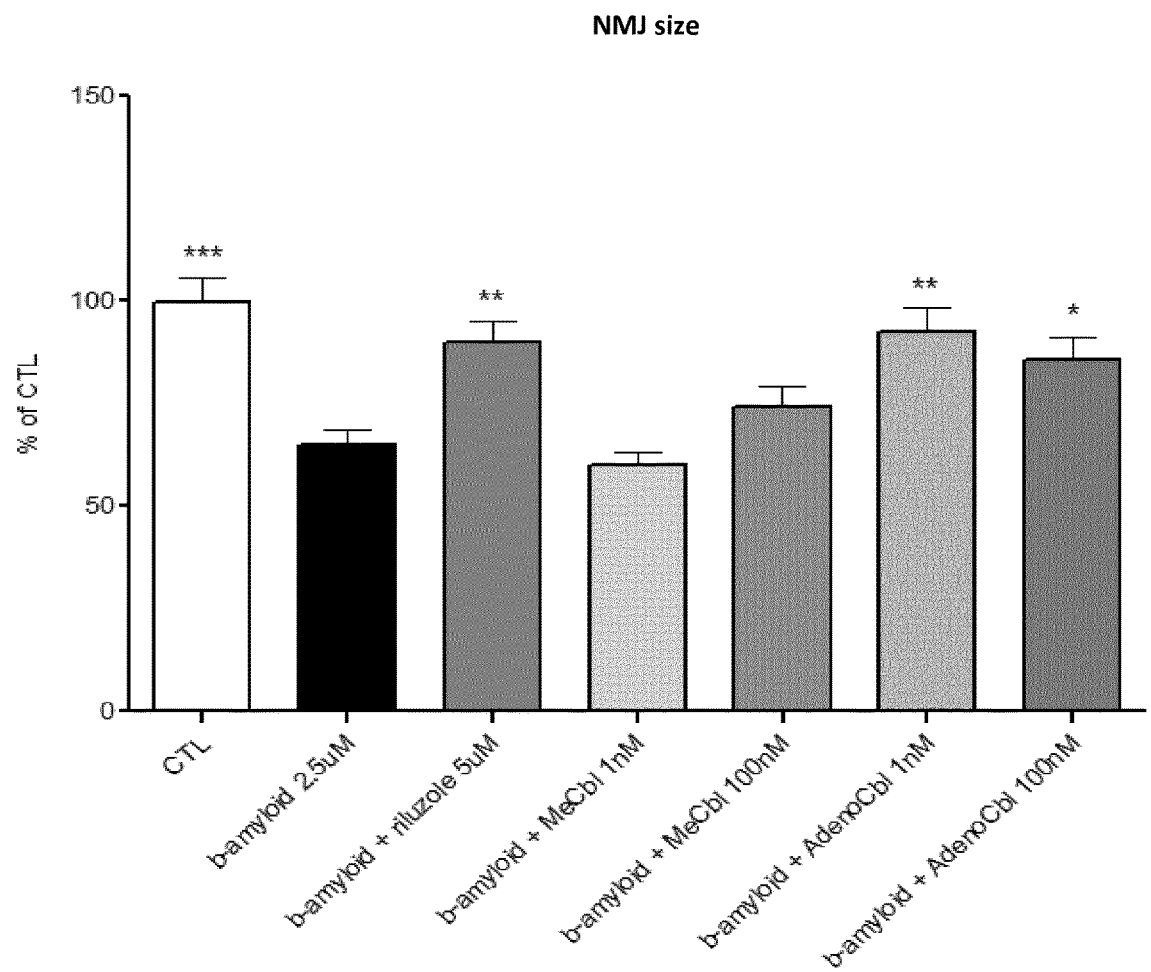
Figure 4B:
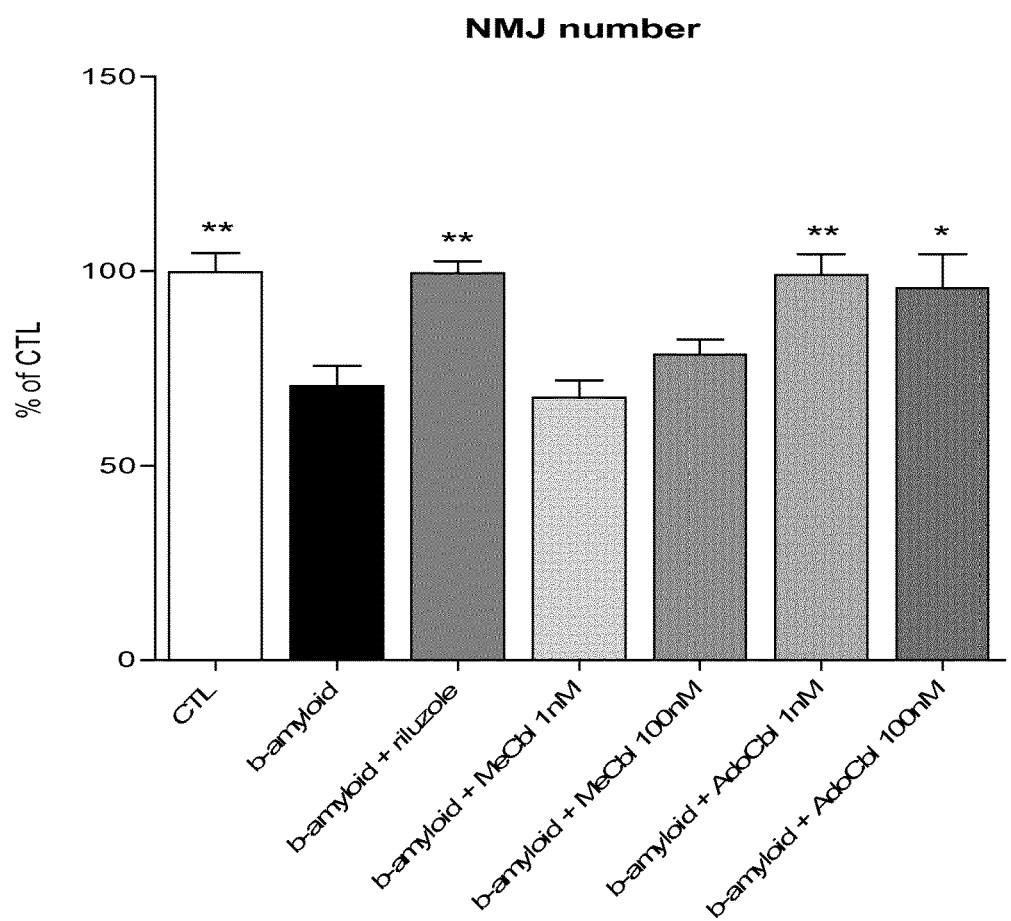
Figure 4C:
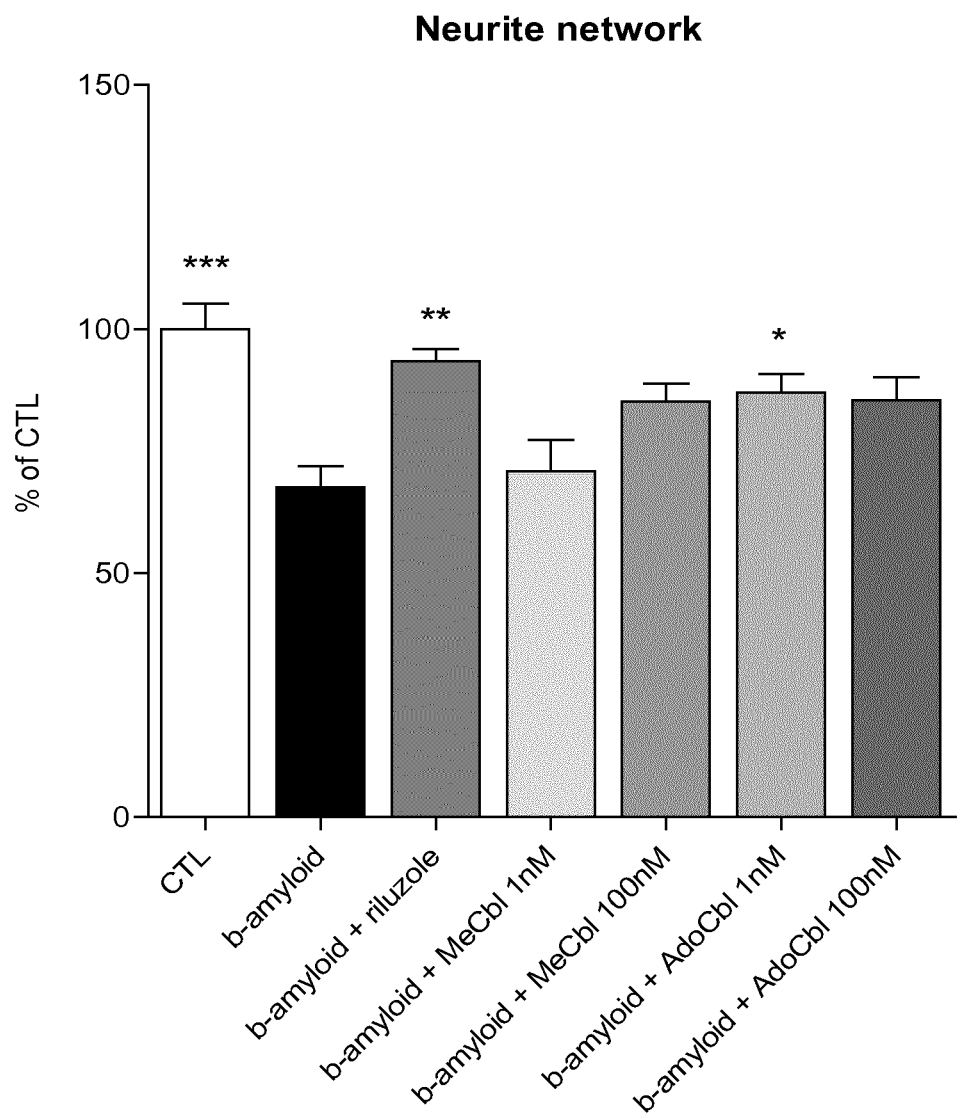

Nerve and muscle co-cultures were grown in vitro until neuromuscular junctions were mature. Damage was induced using beta-amyloid (Ab) incubation (2.5 μM) and riluzole was used as a positive control for preserving neuromuscular junctions from Ab-induced damage. The effect of methyl-cobalamin (MeCbl) and adenosylcobalamin (AdenoCbl) on Ab-induced damage was evaluated by measuring: FIG. 4A the neuromuscular junction (NMJ) size, FIG. 4B the neuromuscular junction number and FIG. 4C the neurite network length. All values are from 6 wells per group and are shown as a percent of the control condition (CTL). =p-value<0.01; *=p-value<0.001.

Figure 5A:
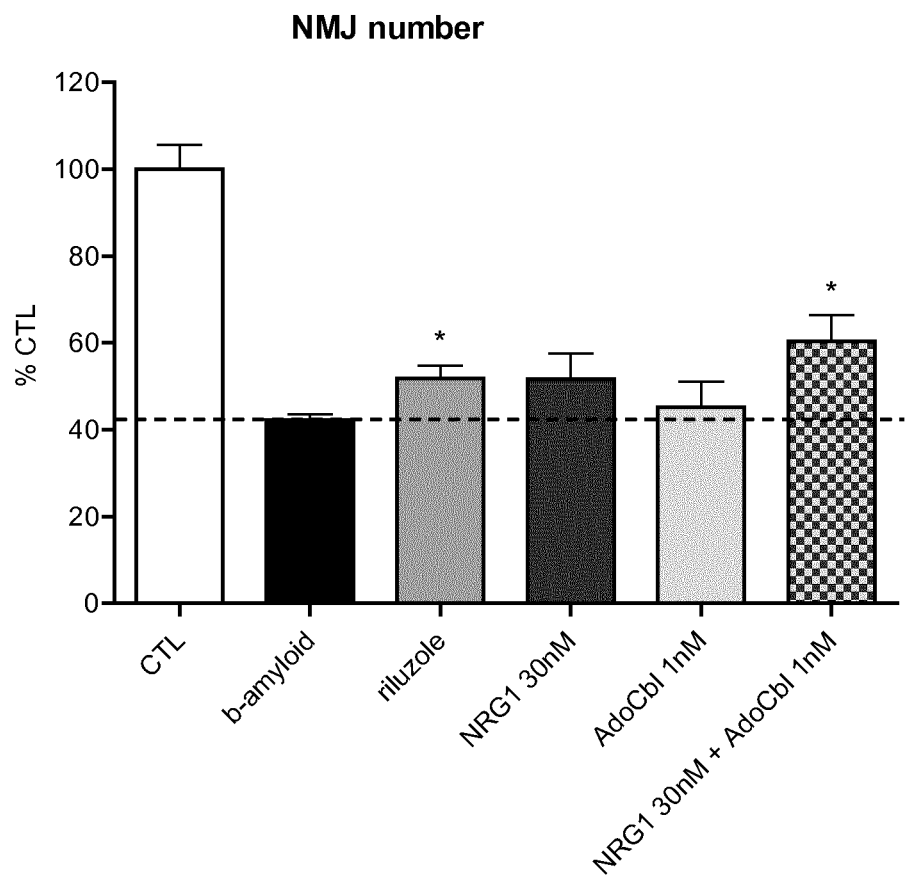
Figure 5B:
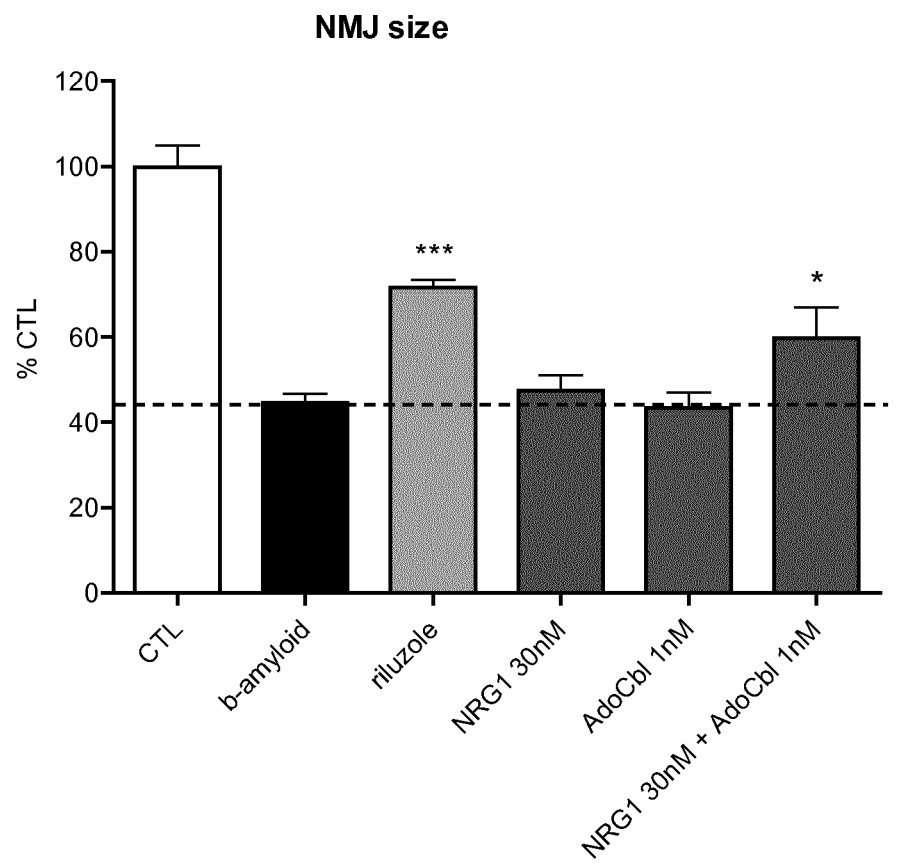

FIGS. 5A and 5B

Neuregulin-1 (NRG1) and Vitamin B12 have Additive Effects on Neuromuscular Junction Protection In Vitro.

Nerve and muscle co-cultures were grown in vitro until neuromuscular junctions were mature. Damage was induced using beta-amyloid (Ab) incubation (10 μM) and riluzole was used as a positive control for preserving neuromuscular junctions from Ab-induced damage. The effect of neuregulin-1 (NRG1) and/or adenosylcobalamin (AdoCbl) on Ab-induced damage was evaluated by measuring the neuromuscular junction (NMJ) number (A) and size (B). All values are from 6 wells per group and are shown as a percent of the control condition (CTL). =p-value<0.01; *=p-value<0.001.

Figure 6A:
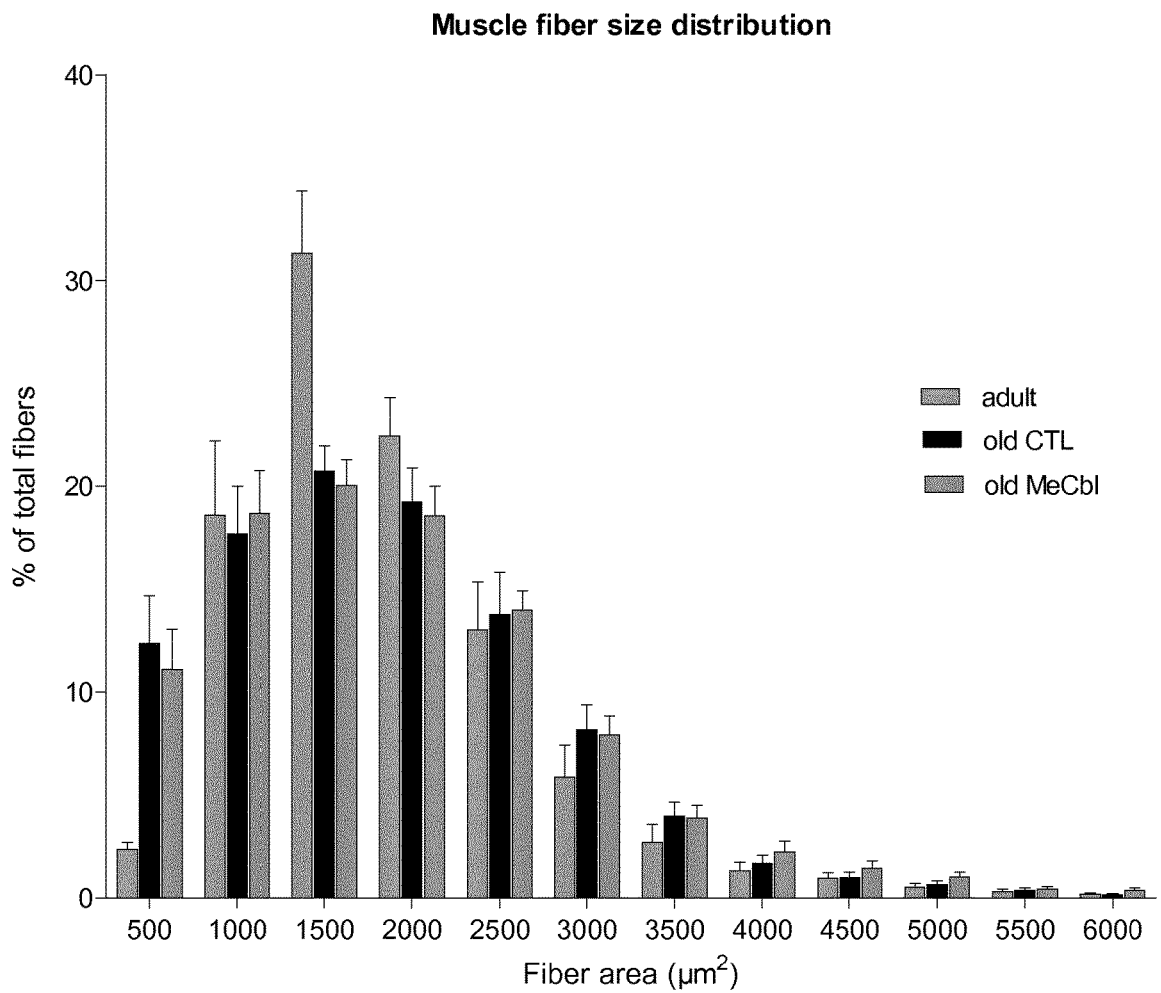
Figure 6B:
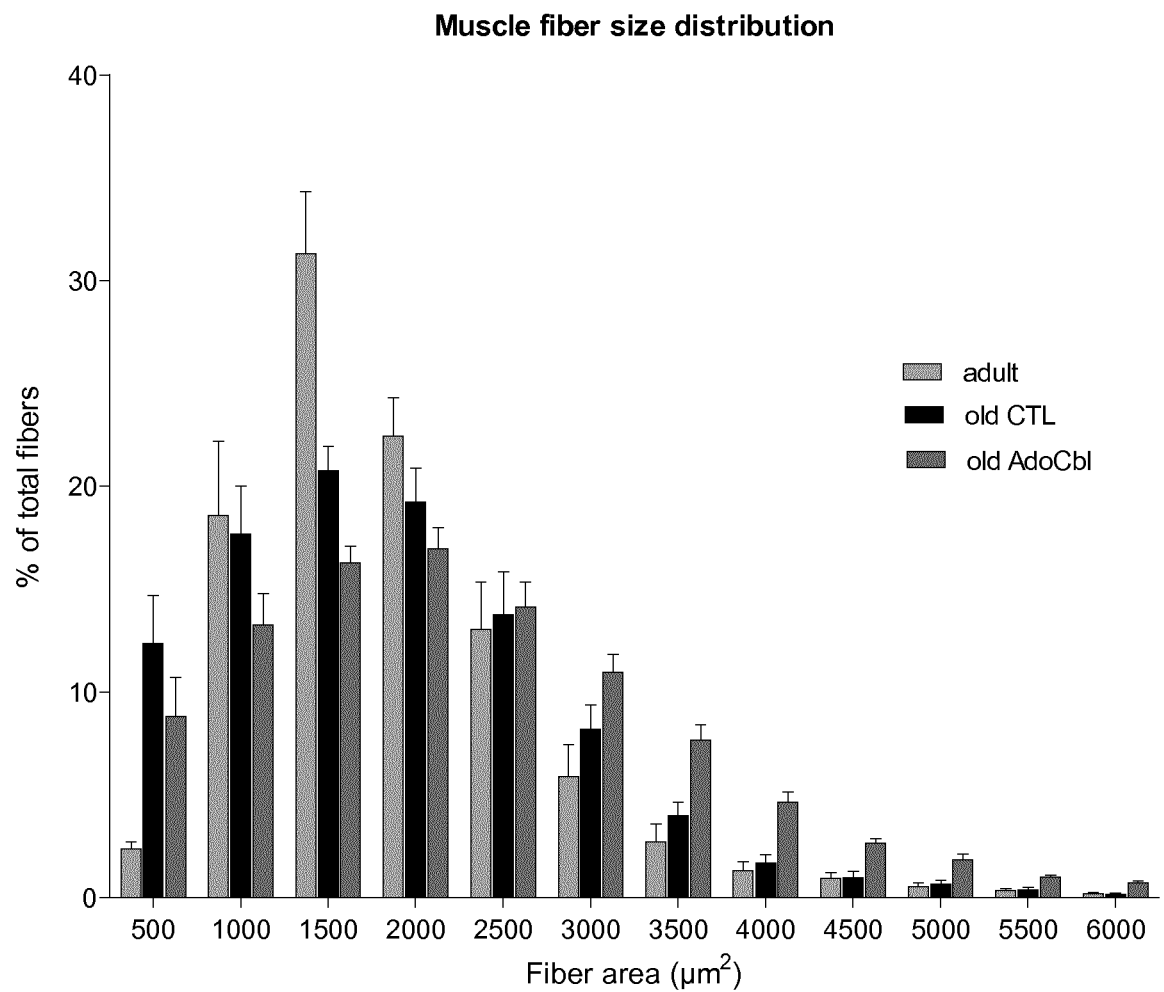

FIGS. 6A and 6B

Adenosylcobalamin Induces an Increase in Muscle Fiber Size in Aged Rats.

Old sarcopenic rats were treated with methyl-cobalamin (MeCbl) in FIG. 6A or adenosyl-cobalamin (AdoCbl) in FIG. 6B for 5 months between 18 and 23 months of age, and compared to age matched sarcopenic controls (old CTL) or young adult healthy controls (adult). Tibialis anterior muscle was dissected out, sectioned and immunostained for fibers. Fiber size distribution for representative type 2A is shown. All values are from 9 animals per group.

FIG. 7

Methylcobalamin Protects from Muscle Atrophy

Human myoblasts were induced to form myotubes in the presence of the atrophic factor TNFa and different forms of vitamin B12 on a 2D+ micro-pattern inducing myotube alignment. IGF is used as a positive control to prevent TNFa-induced atrophy. Fusion index was calculated as the percentage of nuclei inside myotubes (i.e containing ≥2 nuclei) over the total number of nuclei. Values are from 3 wells per group and are shown as a percent of the control condition (CTL). =p-value<0.01 and *=p-value<0.001 compared to CTL condition. ##=p-value<0.01 compared to TNFa condition.

FIGS. 8A-C

Adenosylcobalamin Specifically Reverses Gene Expression Signatures Associated with Sarcopenia while Methylcobalamin Affects Different Gene Expression Signatures in Skeletal Muscle.

Figure 8A:
Figure 8A:
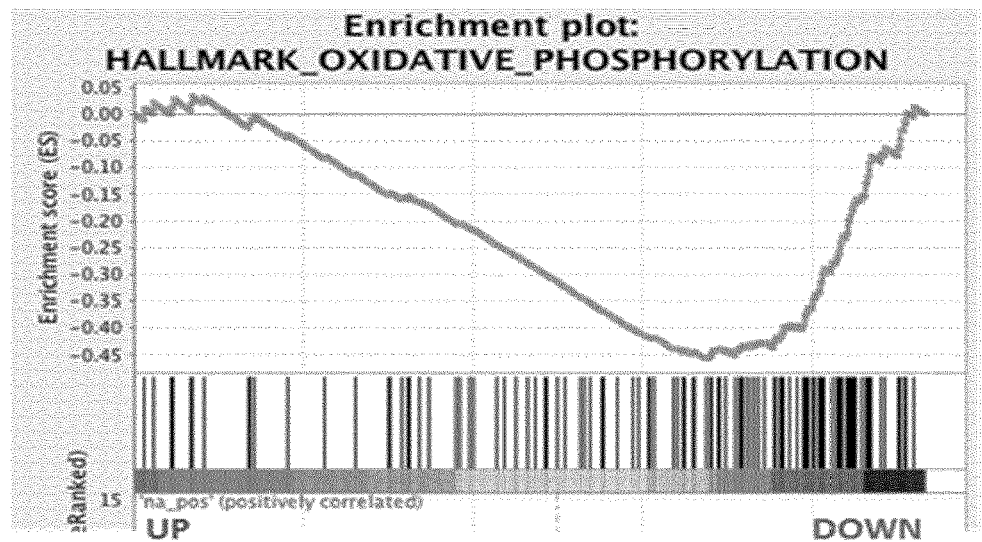
Figure 8B:
Figure 8B:
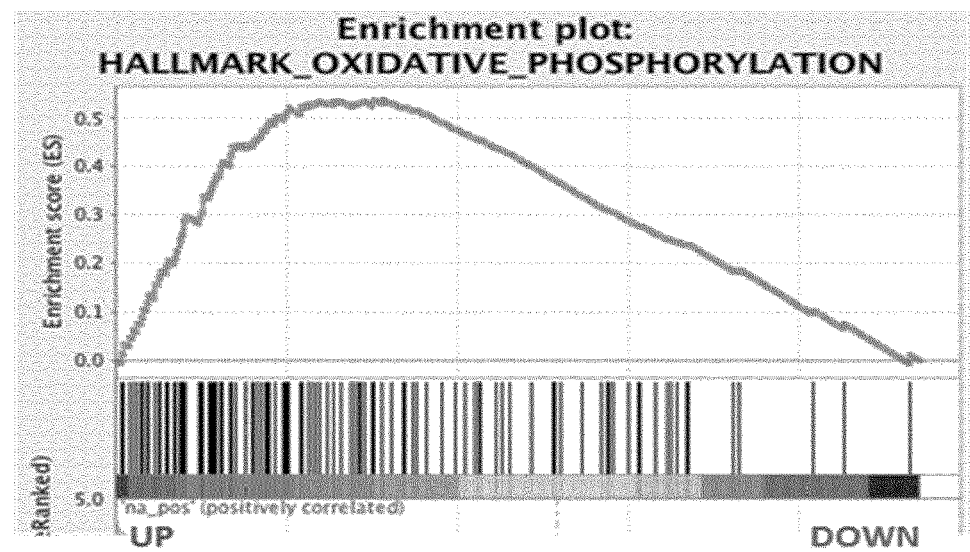
Figure 8C:
Figure 8C:

Old sarcopenic rats were treated with adenosyl-cobalamin (AdoCbl) or methyl-cobalamin (MeCbl) for 5 months between 18 and 23 months of age, and compared to age matched sarcopenic controls (old CTL) or young adult healthy controls (adult). Tibialis anterior muscle was dissected out for RNA extraction and micro-array analysis. GSEA gene enrichments for top regulated pathways in FIG. 8A old controls vs adult, FIG. 8B old treated with adenosyl-cobalamin vs old controls and FIG. 8C old treated with methyl-cobalamin versus old controls are shown.

DETAILED DESCRIPTION OF THE INVENTION

Various preferred features and embodiments of the present invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

Neuregulin

In one aspect, the invention provides neuregulin-1 (NRG1) or a fragment thereof for use in maintaining or increasing muscle function and/or mass in an ageing subject, and/or substantially preventing or reducing muscle wasting in an ageing subject. Neuregulins are a family of soluble and transmembrane growth factors characterised by an EGF-like domain. The neuregulins are mainly expressed by cells of endothelial, neuronal and mesenchymal origin and are involved in a diversity of biological functions such as proliferation, survival or migration.

The neuregulin-1 (NRG1) gene produces six known NRG1 isoforms by alternative splicing, which are termed the type I, II, III, IV, V and VI isoforms. Each isoform contains the EGF-like domain that is necessary for receptor activation. The expression of the different isoforms is spatially and temporally regulated, suggesting that each isoform may have a specific function. All isoforms induce intracellular signaling cascades by acting on specific combinations of the ErbB2, ErbB3 and ErbB4 receptors depending on the isoform (Yarden, Y. et al. (2001) Nat. Rev. Mol. Cell Biol. 2: 127-137).

In one embodiment, the NRG1 or fragment thereof of the invention is human NRG1 or fragment thereof.

In one embodiment, the NRG1 or fragment thereof of the invention is a NRG1 type I, II, III, IV, V or VI isoform.

Preferably, the NRG1 or fragment thereof of the invention is a NRG1 type I isoform. The NRG1 type I isoform may alternatively be known as heregulin (HRG), NEU differentiation factor (NDF) and acetylcholine receptor inducing activity (ARIA).

An example amino acid sequence of the NRG1 HRG-alpha isoform is:

```
                                            (SEQ ID NO: 1)
MSERKEGRGKGKGKKKERGSGKKPESAAGSQSPALPPRLKEMKSQESAAG

SKLVLRCETSSEYSSLRFKWFKNGNELNRKNKPQNIKIQKKPGKSELRIN

KASLADSGEYMCKVISKLGNDSASANITIVESNEIITGMPASTEGAYVSS

ESPIRISVSTEGANTSS
```

An example amino acid sequence of the NRG1 HRG-beta1 isoform is:

```
                                            (SEQ ID NO: 2)
MSERKEGRGKGKGKKKERGSGKKPESAAGSQSPALPPRLKEMKSQESAAG

SKLVLRCETSSEYSSLRFKWFKNGNELNRKNKPQNIKIQKKPGKSELRIN

KASLADSGEYMCKVISKLGNDSASANITIVESNEIITGMPASTEGAYVSS

ESPIRISVSTEGANTSSSTSTSTTGTSHLVKCAEKEKTFCVNGGECFMVK

DLSNPSRYLCKCPNEFTGDRCQNYVMASFYKHLGIEFMEAEELYQKRVLT

ITGICIALLVVGIMCVVAYCKTKKQRKKLHDRLRQSLRSERNNTMNIANG

PHHPNPPPENVQLVNQYVSKNVISSEHIVEREAETSFSTSHYTSTAHHST

TVTQTPSHSWSNGHTESILSESHSVIVMSSVENSRHSSPTGGPRGRLNGT

GGPRECNSFLRHARETPDSYRDSPHSERYVSAMTTPARMSPVDFHTPSSP

KSPPSEMSPPVSSMTVSMPSMAVSPFMEEERPLLLVTPPRLREKKFDHHP

QQFSSFHHNPAHDSNSLPASPLRIVEDEEYETTQEYEPAQEPVKKLANSR

RAKRTKPNGHIANRLEVDSNTSSQSSNSESETEDERVGEDTPFLGIQNPL

AASLEATPAFRLADSRTNPAGRFSTQEEIQARLSSVIANQDPIAV
```

An example amino acid sequence of the NRG1 HRG-beta2 isoform is:

```
                                            (SEQ ID NO: 3)
MSERKEGRGKGKGKKKERGSGKKPESAAGSQSPALPPRLKEMKSQESAAG

SKLVLRCETSSEYSSLRFKWFKNGNELNRKNKPQNIKIQKKPGKSELRIN

KASLADSGEYMCKVISKLGNDSASANITIVESNEIITGMPASTEGAYVSS

ESPIRISVSTEGANTSSSTSTSTTGTSHLVKCAEKEKTFCVNGGECFMVK

DLSNPSRYLCKCPNEFTGDRCQNYVMASFYKAEELYQKRVLTITGICIAL

LVVGIMCVVAYCKTKKQRKKLHDRLRQSLRSERNNTMNIANGPHHPNPPP

ENVQLVNQYVSKNVISSEHIVEREAETSFSTSHYTSTAHHSTTVTQTPSH

SWSNGHTESILSESHSVIVMSSVENSRHSSPTGGPRGRLNGTGGPRECNS

FLRHARETPDSYRDSPHSERYVSAMTTPARMSPVDFHTPSSPKSPPSEMS

PPVSSMTVSMPSMAVSPFMEEERPLLLVTPPRLREKKFDHHPQQFSSFHH

NPAHDSNSLPASPLRIVEDEEYETTQEYEPAQEPVKKLANSRRAKRTKPN

GHIANRLEVDSNTSSQSSNSESETEDERVGEDTPFLGIQNPLAASLEATP

AFRLADSRTNPAGRFSTQEEIQARLSSVIANQDPIAV
```

An example amino acid sequence of the NRG1 HRG-beta3 isoform is:

```
                                            (SEQ ID NO: 4)
MSERKEGRGKGKGKKKERGSGKKPESAAGSQSPALPPRLKEMKSQESAAG

SKLVLRCETSSEYSSLRFKWFKNGNELNRKNKPQNIKIQKKPGKSELRIN

KASLADSGEYMCKVISKLGNDSASANITIVESNEIITGMPASTEGAYVSS

ESPIRISVSTEGANTSSSTSTSTTGTSHLVKCAEKEKTFCVNGGECFMVK

DLSNPSRYLCKCPNEFTGDRCQNYVMASFYSTSTPFLSLPE
```

An example amino acid sequence of the NRG1 HRG-gamma isoform is:

```
                                            (SEQ ID NO: 5)
MSERKEGRGKGKGKKKERGSGKKPESAAGSQSPALPPRLKEMKSQESAAG

SKLVLRCETSSEYSSLRFKWFKNGNELNRKNKPQNIKIQKKPGKSELRIN

KASLADSGEYMCKVISKLGNDSASANITIVESNEIITGMPASTEGAYVSS

ESPIRISVSTEGANTSSSTSTSTTGTSHLVKCAEKEKTFCVNGGECFMVK

DLSNPSRYLCK
```

A further example amino acid sequence of the NRG1 HRG-beta isoform is:

```
                                            (SEQ ID NO: 6)
MSERKEGRGKGKGKKKERGSGKKPESAAGSQSPALPPRLKEMKSQESAAG

SKLVLRCETSSEYSSLRFKWFKNGNELNRKNKPQNIKIQKKPGKSELRIN

KASLADSGEYMCKVISKLGNDSASANITIVESNEIITGMPASTEGAYVSS

ESPIRISVSTEGANTSSSTSTSTTGTSHLVKCAEKEKTFCVNGGECFMVK

DLSNPSRYLCKCPNEFTGDRCQNYVMASFYKHLGIEFMEQKRVLTITGIC

IALLVVGIMCVVAYCKTKKQRKKLHDRLRQSLRSERNNMMNIANGPHHPN
```

An example amino acid sequence of the EGF domain of NRG1 is:

```
                                       (SEQ ID NO: 7; NRG1 beta)
SHLVKCAEKEKTFCVNGGECFMVKDLSNPSRYLCKCPNEFTGDRCQNYVM
ASFYKHLGIEF
```

A further example amino acid sequence of the EGF domain is:

```
                                       (SEQ ID NO: 8; NRG1 alpha)
HLVKCAEKEKTFCVNGGECFMVKDLSNPSRYLCKCQPGFTGARC
```

The NRG1 fragment of the invention is a portion of the full-length polypeptide that maintains the desired function, preferably providing for maintaining or increasing muscle function and/or mass in an ageing subject and/or substantially preventing or reducing muscle wasting in an ageing subject, for example the fragment may substantially retain the natural function of the protein represented by SEQ ID NO: 7. The fragment may substantially retain the natural function of the full-length NRG1.

Preferably, the NRG1 fragment of the invention provides a similar or increased effect of:
 (a) maintaining or increasing muscle function and/or mass in an ageing subject;
 (b) preventing or reducing muscle wasting in an ageing subject; and/or
 (c) treating sarcopenia or frailty,
compared to the protein of SEQ ID NO: 7.

The NRG1 fragment of the invention may be a polypeptide comprising a NRG1 EGF domain, for example an amino acid sequence that has at least 60%, 70%, 80%, 90%, 95%, 96%, 97%, 98%, 99% or 100% identity to SEQ ID NO: 7 or 8, preferably SEQ ID NO: 7, preferably wherein the NRG1 fragment substantially retains the natural function of the protein represented by SEQ ID NO: 7.

In the peripheral nervous system, NRG1 plays a key role in the myelination process both during development and following injury. The myelin lipid-rich sheath surrounding axons allows proper electric signal conduction and velocity, and is produced by the Schwann cells juxtaposed to axons. During the early postnatal development Schwann cells are induced to myelinate upon exogenous cues, one of them being NRG1. The importance of NRG1 for myelination has been shown using mutant mice lacking NRG1 in which nerves display a hypo-myelinated phenotype (Gambarotta, G. et al. (2013) Int. Rev. Neurobiol. 108: 223-256). Similarly, nerve regeneration and re-myelination is incomplete in the absence of neuregulin-1 but is enhanced following neuregulin-1 overexpression or injection (Gambarotta, G. et al. (2013) Int. Rev. Neurobiol. 108: 223-256; Stassart, R. M. et al. (2013) Nat. Neurosci. 16: 48-54; Fricker, F. R. et al. (2011) J. Neurosci. 31: 3225-3233).

At the skeletal muscle level NRG1, has been linked to formation and maintenance of neuromuscular junctions, highly specialised structures allowing the transmission of the electric impulse from the nerve to the muscle for contraction. The vertebrate neuromuscular junction is constituted of a presynaptic nerve terminal provided by a motoneuron, a postsynaptic muscular part made of aggregates of acetylcholine receptors and a terminal Schwann cell. During development, the expression of acetylcholine receptors is induced by NRG1 and their aggregation by neuronal agrin. NRG1 is also thought to be important for neuromuscular junctions maintenance during adulthood. In one study, it was shown that deletion of ErbB2 and ErbB4 in mouse skeletal muscle did not affect neuromuscular junction formation, suggesting that NRG1 could act on the neuromuscular junctions indirectly via Schwann cells.

The NRG1 or fragment thereof of the invention may be administered to a subject in the form of a protein. Suitable routes of administration include sub-cutaneous, intravenous and intramuscular injection.

The NRG1 or fragment thereof of the invention may be administered to a subject via gene therapy. For example, a polynucleotide encoding the NRG1 or fragment thereof of the invention may be introduced into a target cell of the subject. A number of suitable vectors for the delivery of a polynucleotide encoding the NRG1 or fragment thereof of the invention are available, including viral vectors, such as retroviral, lentiviral, adenoviral and adeno-associated viral vectors.

Vitamin B12

In one aspect, the invention provides vitamin B12 for use in maintaining or increasing muscle function and/or mass in an ageing subject, and/or substantially preventing or reducing muscle wasting in an ageing subject.

Vitamin B12 (also known as cobalamine) is a class of cobalt-containing hydrosoluble vitamins which cannot be synthesised by the human body and must therefore be acquired from food or synthesised by the gut microbiota.

The vitamin B12 class may refer to several chemical forms of vitamin B12, depending on the upper axial ligand of the cobalt ion. These are:
 Cyanocobalamin (R=—CN)
 Hydroxocobalamin (R=—OH)
 Methylcobalamin (R=—CH3), and
 Adenosylcobalamin (R=-5'-deoxyadenosyl).

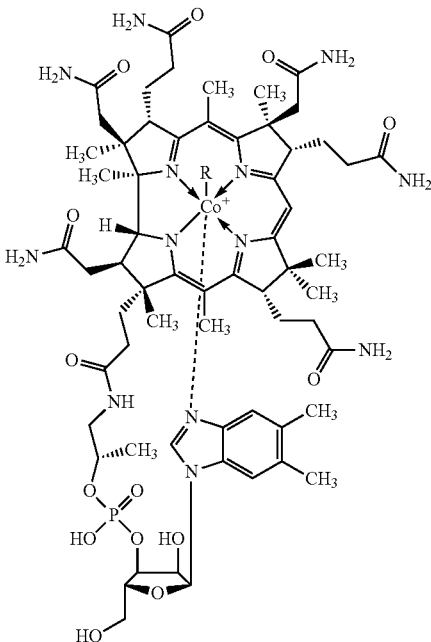

The vitamin B12 pool in the human body is composed of several forms: cyanocobalamin, which is inactive and requires conversion for activity, and methylcobalamin and adenosylcobalamin, which are the metabolically active forms of vitamin B12.

Two enzymes are known to rely on vitamin B12 as a cofactor: methionine synthase and methylmalonylCoA mutase. Methionine synthase is a cytoplasmic enzyme relying on methyl-cobalamine to convert homocysteine to methionine. It thereby plays a critical role in providing S-adenosylmethionine (SAM) as a methylation donor and preventing the toxic accumulation of homocysteine. Low SAM levels and high homocysteine levels observed upon severe vitamin B12 deficiency impair myelination of peripheral nerves and the spinal cord. Methionine synthase also catalyses the activation of 5-methyl-tetrahydrofolate into the bioactive tetrahydrofolate, which is required for 1-carbon metabolism and DNA synthesis, and thus for efficient red blood cell proliferation. MethylmalonylCoA mutase is a mitochondrial enzyme relying on adenosyl-cobalamine to convert methyl-malonylCoA to succinylCoA, which subsequently enters the TCA cycle. It is implicated in the degradation of branched-chain amino acids and odd-chain length fatty acids, and is essential during embryonic life to control neurological development, but is not vital in adult life The vitamin B12 of the invention may be in the form of, for example, vitamin B12 itself, the semi-synthetic derivative cyanocobalamin, hydroxocobalamin, methylcobalamin and/or adenosylcobalamin.

In one embodiment, the vitamin B12 for use according to the present invention is not administered in combination with NRG1 or a fragment thereof as described herein.

The vitamin B12 of the invention may be in the form of, for example, adenosylcobalamin, methylcobalamin, cyanocobalamin and/or hydroxocobalamin.

In one embodiment, the vitamin B12 may be adenosylcobalamin and/or methylcobalamin. In a preferred embodiment, the vitamin B12 may be adenosylcobalamin.

In one embodiment the adenosylcobalamin maintains or increases muscle mass, for example in one embodiment, the adenosylcobalamin increases muscle fibre size.

In one aspect the present invention provides the use of adenosylcobalamin for increasing maintaining or increasing muscle mass in an ageing subject.

In another aspect the present invention provides a method for maintaining or increasing muscle mass in an ageing subject, which comprises the step of administering adenosylcobalamin to an ageing subject in need thereof.

In one aspect the present invention provides the use of adenosylcobalamin in the manufacture of a medicament for maintaining or increasing muscle mass in an ageing subject.

In some embodiments described herein, the adenosylcobalamin maintains or increases muscle size by maintaining or increasing muscle fiber size.

In one embodiment the methylcobalamin substantially prevents or reduces muscle wasting. As used herein, muscle wasting may be synonymous with 'muscle atrophy' and is used to refer to a decrease in the mass of muscle. In one embodiment reducing muscle atrophy may therefore be synonymous with maintaining muscle mass.

In one aspect the present invention provides the use of methylcobalamin for substantially preventing or reducing muscle atrophy in an ageing subject.

In another aspect the present invention provides a method for substantially preventing or reducing muscle atrophy in an ageing subject, which comprises the step of administering methylcobalamin to an ageing subject in need thereof.

In one aspect the present invention provides the use of methylcobalamin in the manufacture of a medicament for substantially preventing or reducing muscle atrophy in an ageing subject.

In one embodiment the present invention provides a combination of adenosylcobalamin and methylcobalamin for use in maintaining or increasing muscle mass and substantially preventing or reducing muscle wasting in an ageing subject.

The vitamin B12 of the invention may be administered to a subject by any suitable route, for example orally, intranasally, intravenously, parentally, sub-linguially, sub-cutaneously, transdermally or intramuscularly.

In another aspect the present invention provides a method of treating sarcopenia or frailty comprising administering vitamin B12 to a subject in need thereof.

In a further aspect the present invention provides the use of vitamin B12 as described herein for the manufacture of a medicament for:
 (a) maintaining or increasing muscle function and/or mass in an ageing subject;
 (b) substantially preventing or reducing muscle wasting in an ageing subject; and/or
 (c) treating sarcopenia or frailty.

Vitamin B12 Deficiency

In one embodiment the subject may be vitamin B12 deficient.

The Recommended dietary allowance (RDA) of US adults was set at 2.4 µg per day by the Institute of Medicine, based on an average absorption from food of ~50% (National Academy of Sciences, Institute of Medicine (2000); Dietary Reference Intakes for Thiamin, Riboflavin, Niacin, Vitamin B6, Folate, Vitamin B12, Pantothenic Acid, Biotin and Choline, Chapter 9, pp 306-56). It was noted that the daily requirement varies with body size.

The likelihood of vitamin B12 deficiency in humans may be defined according to the serum vitamin B12 level as follows: <148 picomols/L (<200 picograms/mL) indicates probable deficiency, 148 to 258 picomols/L (201 to 350 picograms/mL) indicates possible deficiency and >258 picomols/L (>350 picograms/mL) indicates that deficiency is unlikely (BMJ, Best Practice, http://bestpractice.bmj.com/best-practice/monograph/822/basics.html). However, because of the lack of a gold standard for determining vitamin B12 levels and related complications regarding active and inactive vitamin B12, assays of serum vitamin B12 are often combined with further biochemical assays or clinical assessment based on presenting symptoms, in order to diagnose vitamin B12 deficiency.

Additional assays which may be performed to give a further indication of a vitamin B12 deficiency include determining the level of, holotranscobalamine, methylmalonic acid and/or homocysteine in a sample isolated from the subject.

Holotranscobalamin refers to vitamin B12 bound to its bioactive serum transporter transcobalamine II. Holotranscobalamin levels may be determined using commercial available assays (e.g. ELISA assays). Low levels of holotranscobalamin are associated with a potential vitamin B12 deficiency.

Methyl-malonic acid (MMA) accumulates with low activity of the vitamin B12-dependent enzyme methylmalonyl-CoA mutase. As such high levels of MMA are associated with vitamin B12 deficiency.

Homocysteine accumulates with low activity of the vitamin B12-dependent enzyme methionine synthase. Low High levels of homocysteine are associated with vitamin B12 deficiency. However assays of homocysteine levels can be confounded by folate deficiency.

Vitamin B12 may, for example, be provided in the form of a tablet, liquid (e.g. for ingestion, or use in a nasal spray or injection) or transdermal patch. For example, vitamin B12 is available as a nutritional supplement either on its own or in combination with other supplements.

Oral supplementation typically involves giving 250 µg to 1 mg of vitamin B12 daily.

The present invention may comprise administering a probiotic supplement comprising vitamin B12 producing bacteria to a subject.

The probiotic supplement can include any probiotic microorganism(s) which beneficially affect the host subject by improving its intestinal microbial balance to enhance vitamin B12 uptake. The probiotic microorganism can be selected from the group comprising of *Bifidobacterium, Lactobacillus, Streptococcus, Enterococcus* and *Saccharomyces* or mixtures thereof.

Certain probiotic microorganisms which are native components of the gut microbiota are known to produce vitamin B12, for example, lactic acid producing bacteria such as *Lactobacillus. delbrueckii* subsp. *bulgaricus* (see Le Blanc et al.; J App. Micro.; 111(6); (2011)). Advantageously, the probiotic supplement can enhance existing microorganisms in the gut that produce vitamin B12 in situ.

The oral vitamin B12 supplementation may be in the form of a food or beverage product. The food or beverage product may comprise a probiotic supplement comprising vitamin B12 producing bacteria or other probiotics which can enhance existing microorganisms in the gut that produce vitamin B12 in situ.

Typically, a physician will determine the actual dosage which will be most suitable for an individual subject and it will vary with the age, weight and response of the particular patient. The dosage is such that it is sufficient to provide required levels of active vitamin B12.

In one aspect, the invention provides a combined preparation of neuregulin-1 (NRG1) or a fragment thereof of the invention and vitamin B12, wherein the NRG1 or fragment thereof and vitamin B12 are for simultaneous, combined, sequential or separate administration to a subject.

By "simultaneous", it is to be understood that the two agents are administered concurrently, whereas the term "combined" is used to mean they are administered, if not simultaneously, then "sequentially" within a time frame that they both are available to act therapeutically within the same time frame. Thus, administration "sequentially" may permit one agent to be administered within 5 minutes, 10 minutes or a matter of hours after the other provided the circulatory half-life of the first administered agent is such that they are both concurrently present in therapeutically effective amounts. The time delay between administration of the components will vary depending on the exact nature of the components, the interaction there-between, and their respective half-lives.

In contrast to "combined" or "sequential", "separate" is to be understood as meaning that the gap between administering one agent and the other agent is significant, i.e. the first administered agent may no longer be present in the bloodstream in a therapeutically effective amount when the second agent is administered.

Muscle Function and Mass

The compounds, compositions, uses and methods of the invention may provide for the maintenance of or increase in muscle function and/or mass in an ageing subject.

The term "muscle function" refers to the ability of a muscle to perform in a manner that does not negatively impact on the life of a subject, and encompasses parameters of muscle strength, muscle contraction, muscle endurance and/or muscle elasticity.

Suitable tests for assessing muscle function include grip strength assessment using a dynamometer; one repeat maximum on leg press, chest press or leg extension; gait speed; 6 min walk test; time up and go; short physical performance battery; Fried frailty criteria; and stair climbing time assessments.

Muscle mass (which may equate with muscle volume, muscle thickness or myofiber/muscle fiber size) may be measured by dual-energy X-ray absorptiometry (DXA) or bioimpedance tests. Similarly, MRI may be used for assessing muscle volume and ultra-sound may be used for assessing muscle thickness and pennation angle.

Preferably, the compounds, compositions, uses and methods of the invention provide for the maintenance of or increase in muscle mass in an ageing subject The term "maintains" refers to a particular parameter, such as muscle function and/or mass, remaining substantially unchanged over a period of time (e.g. 5, 10, 15, 20, 25, 30, 40, 50 or more years).

In one embodiment, muscle mass increases by at least 1%, 2%, 3%, 4%, 5%, 10%, 15% or 20%.

In another embodiment, muscle mass increases by 1-2.5%, 1-5%, 1-10% or 1-20%.

Preferably, the muscle is skeletal muscle.

Method of Treatment

It is to be appreciated that all references herein to treatment include curative, palliative and prophylactic treatment; although in the context of the invention references to preventing are more commonly associated with prophylactic treatment. Treatment may also include arresting progression in the severity of a disease.

Subject

The treatment of mammals, particularly humans, is preferred. However, both human and veterinary treatments are within the scope of the invention.

The ageing subjects to be treated may, for example, be a human subject over the age of 30, 35, 40, 45, 50, 55, 60, 65, 70, 75, 80, 85, 90, 95 or 100 years old. For veterinary applications, the age of the animal would be scaled from the human situation using the average lifespan for calibration.

In embodiments of the present invention the NRG1 or a fragment thereof or the vitamin B12 is administered to an ageing subject as a medicament in order to maintain or increase muscle function, and/or substantially prevent or reduce muscle wasting, and/or to treat sarcopenia or frailty, wherein the subject has reduced muscle mass and/or muscle function which causes debilitation and/or a negative impact on the subject's quality of life.

Sarcopenia and Frailty

The invention provides a means to address loss of muscle function and mass that occurs with age. Age-related loss of muscle function and mass occurs inevitably in all individuals, however its progression depends on a range of genetic and environmental factors, such as physical activity and nutritional intake.

The specific condition of sarcopenia is defined as occurring at the point at which the age-related loss of muscle mass and function becomes debilitating and impacts on quality of life (Sayer, A. A. et al. (2013) Age Ageing 42: 145-150). In contrast, frailty is a classification of age-related muscle dysfunction which relies on muscle strength and functionality, but not muscle mass (Morley, J. E. et al. (2013) J. Am. Med. Dir. Assoc. 14: 392-397).

Sarcopenia and frailty are multi-factorial syndromes which associate with pathophysiological changes, such as impaired neuro-muscular transition, altered excitation/contraction coupling, impaired regenerative capacity linked to stem cell exhaustion, defects of mitochondrial and energy metabolism in myofibers, and marbling of skeletal muscle with fat and fibrosis (Ali, S. et al. (2014) Gerontology 60: 294-305). The aetiology of these syndromes is therefore complex and poorly understood, but low physical activity, hormonal decline in anabolic hormones (e.g. androgens and IGF-1), and malnutrition and/or nutritional deficiencies play an important role (Mithal, A. et al. (2013) Osteoporos. Int. 24: 1555-1566).

Method of Screening

In one aspect, the invention provides a method of screening for an agent capable of increasing neuregulin-1 (NRG1) levels in a subject. The method may comprise the steps:

(a) contacting a population of cells with a candidate agent;
(b) determining the level of NRG1 in the population of cells; and
(c) comparing the level of NRG1 determined in step (b) with a NRG1 level in a control population of cells which has not been contacted with the candidate agent.

Preferably, the method is an in vitro method.

The candidate agent may, for example be a pharmaceutical agent or nutritional supplement. Preferably, the candidate agent is a nutritional supplement.

In one embodiment, the candidate agent is comprised in a library of candidate agents.

In one embodiment, the population of cells is a population of nerve (e.g. nerve Schwann cells, in particular rat primary cells) or muscle cells (e.g. the C2C12 cell line and/or human primary myoblasts). In another embodiment, the population of cells is a combined population of nerve and muscle cells.

The term "level of NRG1" refers to the amount of NRG1 protein that is found in a sample. The amount of NRG1 protein may be determined directly or indirectly. Direct methods of determining NRG1 include SDS-PAGE, Western blotting, chromatographic methods (e.g. HPLC or FPLC), mass spectrometry-based methods (e.g. LC/MS) and NMR. Indirect methods of determining NRG1 include methods based on the detection of NRG1-encoding nucleic acids, in particular mRNAs, such as qPCR.

The effect of the candidate agent on NRG1 levels may be assessed as a function of time, by carrying out repeated measurements over a particular time-course.

Candidate agents may also be analysed (e.g. as a validation in a subsequent step of the screening method) for their effect on myelination in a Schwann cell/motor neuron co-culture system.

Example screening methods include:
(a) Muscle cell-based screen (e.g. C2C12 cell line and/or human primary myoblasts): Cells may be grown to 90% confluence and induced to differentiate for up to 14 days. Candidate agents may be added to the medium for 1-2 days and NRG1 expression may be evaluated by qPCR.
(b) Nerve Schwann cell-based screen (rat primary cells). Cells may be grown in proliferating conditions and candidate agents may be added to the medium for 1-2 days. NRG1 expression may be evaluated by qPCR.
(c) Candidate agents may also be tested in a co-culture system (Schwann cells/motor neurons) to evaluate myelination.

Example candidate agents may include lipoic acid, vitamin B12 derivatives, HDAC inhibitors and/or traditional Chinese medicine components.

Method of Diagnosis

In one aspect, the invention provides a method of diagnosing sarcopenia or frailty comprising the steps:
(a) providing a biological sample isolated from a subject;
(b) determining the level of neuregulin-1 (NRG1) in the biological sample; and
(c) comparing the level of NRG1 determined in step (b) with a NRG1 level determined from one or more control samples or reference levels.

The one or more control samples may be isolated from a subject with or without sarcopenia or frailty. Accordingly, comparison with such control samples may provide an indication of the subject having sarcopenia or frailty, or deteriorating towards the state of sarcopenia or frailty.

Alternatively or additionally, a level of NRG1 below a pre-determined reference level may indicate the subject has sarcopenia or frailty, while a level of NRG1 above a different pre-determined reference level may indicate the subject does not have sarcopenia or frailty.

The term "level of NRG1" refers to the amount of NRG1 protein that is found in a sample. The amount of NRG1 protein may be determined directly or indirectly. Direct methods of determining NRG1 include SDS-PAGE, Western blotting, chromatographic methods (e.g. HPLC or FPLC), mass spectrometry-based methods (e.g. LC/MS) and NMR. Indirect methods of determining NRG1 include methods based on the detection of NRG1-encoding nucleic acids, in particular mRNAs, such as qPCR.

The biological sample may be any suitable sample for isolating from the body of a subject, such as a blood sample (e.g. plasma or serum) or tissue biopsy (in particular a muscle biopsy).

In one embodiment, the method may comprise a further step of administering the NRG1 or fragment thereof of the invention to the subject, wherein the subject has been diagnosed as having sarcopenia or at being risk of developing sarcopenia, or diagnosed as being frail or at being risk of becoming frail.

In another embodiment, the method may comprise a further step of applying a dietary intervention for maintaining or increasing muscle function and/or mass wherein the subject has been diagnosed as having sarcopenia or being at risk of developing sarcopenia, or diagnosed as being frail or at being risk of becoming frail. Preferably, the dietary intervention is for maintaining or increasing muscle mass. Example dietary interventions include high protein and/or carbohydrate diets.

In another aspect, the invention provides a method of diagnosing loss of muscle function and/or mass with age comprising the steps:
(a) providing a biological sample isolated from a subject;
(b) determining the level of neuregulin-1 (NRG1) in the biological sample; and
(c) comparing the level of NRG1 determined in step (b) with a NRG1 level determined from one or more control samples or reference levels.

The loss of muscle function and/or mass may be associated with sarcopenia or frailty.

In another aspect, the invention provides a method of selecting a dietary intervention comprising the steps:
(a) providing a biological sample isolated from a subject;
(b) determining the level of neuregulin-1 (NRG1) in the biological sample;
(c) comparing the level of NRG1 determined in step (b) with a NRG1 level determined from one or more control samples or reference levels; and
(d) applying a dietary intervention for maintaining or increasing muscle function and/or mass wherein the subject has been diagnosed as having sarcopenia or being at risk of developing sarcopenia, or diagnosed as being frail or at being risk of becoming frail.

Preferably, the dietary intervention is for maintaining or increasing muscle mass. Example dietary interventions include high protein and/or carbohydrate diets, and vitamin B12 and/or vitamin D supplements.

A control sample may be from the same subject, taken at an earlier time point. Similarly, a reference level may be determined based on previous analyses carried out on the same subject. Accordingly in another aspect, the invention provides a method of determining the progression of sarcopenia or frailty in a subject comprising the steps:
(a) providing a biological sample isolated from a subject;
(b) determining the level of neuregulin-1 (NRG1) in the biological sample; and
(c) comparing the level of NRG1 determined in step (b) with a NRG1 level determined from a sample taken from the same subject at an earlier time.

Dietary Intervention and Product

The term "dietary intervention" refers to an external factor applied to a subject which causes a change in the subject's diet. In one embodiment, the dietary intervention is a high calorie diet. In another embodiment, the dietary intervention is a high protein and/or carbohydrate diet. In another embodiment, the dietary intervention is a diet supplemented with vitamins and minerals, in particular vitamin B12 and/or vitamin D.

In a preferred embodiment, the dietary intervention is a diet supplemented with vitamin B12, in particular adenosylcobalamin and/or methylcobalamin.

In another preferred embodiment, the dietary intervention is a diet supplemented with vitamin B12, in particular hydroxocobalamin and/or cyanocobalamin which can be converted into methylcobalamin and/or adenosylcobalamin.

The diet may be one which is adjusted to the starting body weight of the subject.

The dietary intervention may comprise administration of at least one diet product. The diet product may be a meal replacement product or a supplement product which may, for example, increase the subject's appetite. The diet product may include food products, drinks, pet food products, food supplements, nutraceuticals, food additives or nutritional formulas. Example oral nutritional supplements include Nestle Boost and Meritene products.

Variants, Derivatives, Analogues, Homologues and Fragments

In addition to the specific proteins and nucleotides mentioned herein, the invention also encompasses the use of variants, derivatives, analogues, homologues and fragments thereof.

In the context of the invention, a variant of any given sequence is a sequence in which the specific sequence of residues (whether amino acid or nucleic acid residues) has been modified in such a manner that the polypeptide or polynucleotide in question substantially retains its function. A variant sequence can be obtained by addition, deletion, substitution, modification, replacement and/or variation of at least one residue present in the naturally-occurring protein.

The term "derivative" as used herein, in relation to proteins or polypeptides of the invention includes any substitution of, variation of, modification of, replacement of, deletion of and/or addition of one (or more) amino acid residues from or to the sequence providing that the resultant protein or polypeptide substantially retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics.

Typically, amino acid substitutions may be made, for example from 1, 2 or 3 to 10 or 20 substitutions provided that the modified sequence substantially retains the required activity or ability. Amino acid substitutions may include the use of non-naturally occurring analogues.

Proteins used in the invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity and/or the amphipathic nature of the residues as long as the endogenous function is retained. For example, negatively charged amino acids include aspartic acid and glutamic acid; positively charged amino acids include lysine and arginine; and amino acids with uncharged polar head groups having similar hydrophilicity values include asparagine, glutamine, serine, threonine and tyrosine.

Conservative substitutions may be made, for example according to the table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R H |
| AROMATIC | | F W Y |

The term "homologue" as used herein means an entity having a certain homology with the wild type amino acid sequence and the wild type nucleotide sequence. The term "homology" can be equated with "identity".

A homologous sequence may include an amino acid sequence which may be at least 50%, 55%, 60%, 65%, 70%, 75%, 80%, 85% or 90% identical, preferably at least 95% or 97% or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the invention it is preferred to express homology in terms of sequence identity.

A homologous sequence may include a nucleotide sequence which may be at least 50%, 55%, 60%, 65%, 70%, 75%, 80%, 85% or 90% identical, preferably at least 95% or 97% or 99% identical to the subject sequence. Although homology can also be considered in terms of similarity, in the context of the invention it is preferred to express homology in terms of sequence identity.

Preferably, reference to a sequence which has a percent identity to any one of the SEQ ID NOs detailed herein refers to a sequence which has the stated percent identity over the entire length of the SEQ ID NO referred to.

Homology comparisons can be conducted by eye or, more usually, with the aid of readily available sequence comparison programs. These commercially available computer programs can calculate percentage homology or identity between two or more sequences.

Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion in the nucleotide sequence may cause the following codons to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum percentage homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al. (1984) Nucleic Acids Res. 12: 387). Examples of other software that can perform sequence comparisons include, but are not limited to, the BLAST package (see Ausubel et al. (1999) ibid—Ch. 18), FASTA (Atschul et al. (1990) J. Mol. Biol. 403-410) and the GENEWORKS suite of comparison tools. Both BLAST and FASTA are available for offline and online searching (see Ausubel et al. (1999) ibid, pages 7-58 to 7-60). However, for some applications, it is preferred to use the GCG Bestfit program. Another tool, called BLAST 2 Sequences is also available for comparing protein and nucleotide sequences (see FEMS Microbiol. Lett. (1999) 174: 247-50; FEMS Microbiol. Lett. (1999) 177: 187-8).

Although the final percent homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see the user manual for further details). For some applications, it is preferred to use the public default values for the GCG package, or in the case of other software, the default matrix, such as BLOSUM62.

Once the software has produced an optimal alignment, it is possible to calculate percent homology, preferably percent sequence identity. The software typically does this as part of the sequence comparison and generates a numerical result.

"Fragments" of neuregulin-1 (NRG1) are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site may be made. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

EXAMPLES

Example 1

Materials and Methods

Variation of Circulating Levels of Neuregulin-1 (NRG1) with Age in Rats.

Neuregulin-1 (NRG1, in particular the NRG1 beta EGF domain) levels were measured in serum from rats aged 8 months, 18 months or 24 months using slow off-rate DNA aptamer detection (Gold, L. et al. (2010) PLoS ONE 5: e15004). 10 animals per group were analysed.

Effect of Neuregulin-1 (NRG1) on Neuromuscular Junctions In Vitro.

Nerve and muscle co-cultures were grown in vitro until neuromuscular junctions were mature. Damage was induced using beta-amyloid (Ab) incubation (2.5 µM) and riluzole (5 µM) was used as a positive control for preserving neuromuscular junctions from Ab-induced damage.

The effect of neuregulin-1 (NRG1; various concentrations, as specified in FIG. 2) on Ab-induced damage was evaluated by measuring the neuromuscular junction (NMJ) size. 6 wells per group were analysed and compared to a control condition. The uninjured control condition is the neuromuscular junction size without Ab treatment. All other conditions are to be compared to the Ab treatment alone which represents the reference value for damaged neuromuscular junction size.

Effect of Neuregulin-1 (NRG1) on Age-Induced Atrophy of Skeletal Muscle.

Pre-sarcopenic rats aged 16 months were treated for 5 months with either neuregulin-1 (NRG1; NRG1 beta EGF domain from Reprokine (catalog number RKQ02297)) or saline. NRG1 was injected sub-cutaneously at 1 µg/kg body weight 3 time per week. Hind-limb skeletal muscle mass was then evaluated and compared to a group of adult healthy rats (8 months at start of experiment) injected with saline control. Hind-limb skeletal muscle mass was then evaluated and compared to an adult healthy group of rats.

Effect of Vitamin B12 on Neuromuscular Junctions In Vitro.

Nerve and muscle co-cultures were grown in vitro until neuromuscular junctions were mature. Damage was induced using beta-amyloid (Ab) incubation (2.5 µM) and riluzole (5 µM) was used as a positive control for preserving neuromuscular junctions from Ab-induced damage. The effect of methylcobalamin (MeCbl; 1 or 100 nM) and adenosylcobalamin (AdenoCbl; 1 or 100 nM) on Ab-induced damage was evaluated by measuring the neuromuscular junction (NMJ) number and size, and the neurite network. 6 wells per group were analysed and compared to a control condition (CTL). The uninjured control condition is the neuromuscular junction size without Ab treatment. All other conditions are to be compared to the Ab treatment alone which represents the reference value for damaged neuromuscular junction size.

Effect of Vitamin B12 on Skeletal Muscle In Vivo.

Pre-sarcopenic rats aged 16 months were treated for 5 months with either adenosylcobalamin (AdoCbl, C0884, Sigma aldrich), methylcobalamin (MeCbl, M9756, Sigma aldrich) or saline. AdoCbl and MeCbl were injected sub-cutaneously at 1 mg/kg body weight 3 time per week. Tibialis Anterior (TA) was then dissected out and frozen for further analyses. For histology, TA was cryo-sectioned at 10 µm and stained with laminin (L9393, Sigma aldrich) to delineate fibers. Specific fiber types 1, 2A and 2B were immunolabeled subsequently with appropriate antibodies (clones BADS, BFF3, and SC71 respectively, DSHB).

Images were acquired using a slide scanner (VS-120, Olympus) and analyzed using an in-house MetaXpress journal (Molecular Devices, Sunnyvale, USA). Images from old animals were compared to a group of adult healthy rats (8 months at start of experiment) injected with saline control. For gene expression analysis, total RNA was extracted using the miRNeasy Mini Kit (Qiagen) according to the manufacturer's instruction and RNA quality was checked using the Standard Sensitivity RNA Analysis Kit on a Fragment Analyzer (Advanced Analytical Technologies). Samples were then hybridized on Affymetrix Rat 230 PM 96-Array following standard Affymetrix protocol, based on the Eberwine T7 procedure. Statistical analysis was performed using LIMMA and exploited in GSEA to compare old control animals versus adult animals, and old animals treated with either AdoCbl or MeCbl versus old control animals.

Effect of Vitamin B12 on Protection from Muscle Atrophy

HSMM human myoblasts were grown in vitro and induced to differentiate into mature myotubes. Myotube atrophy was induced by incubation with TNFa at 40 ng/ml for 4 days. MeCbl (1 nM) and AdoCbl (1 nM) were incubated together with TNFa to test their effect on induced atrophy. IGF1 is used as a positive control at 15 nM to prevent muscle atrophy. After 4 days of treatment, cells were stained for nuclei and myosin heavy chain to quantify the proportion of nuclei inside myotubes (i.e fusion index).

Effect of Neuregulin-1 (NRG1) and Vitamin B12 on Neuromuscular Junctions In Vitro.

Nerve and muscle co-cultures were grown in vitro until neuromuscular junctions were mature. Damage was induced using beta-amyloid (Ab) incubation (10 µM) and riluzole (5 µM) was used as a positive control for preserving neuromuscular junctions from Ab-induced damage. The effect of neuregulin-1 (NRG1; 30 nM) and/or adenosylcobalamin (AdoCbl; 1 nM) on Ab-induced damage was evaluated by measuring the neuromuscular junction (NMJ) size or number. 6 wells per group were analysed and compared to a control condition (CTL) without Ab-induced damage.

Results

Using an aptamer-based screen (Somalogic) on serum from rats aged 8 months, 18 months or 24 months, we found that neuregulin-1 (NRG1) circulating levels decrease with age (FIG. 1). This decrease is concomitant with the progression of sarcopenia.

Considering that neuregulin-1 plays major roles both at the nerve and the neuromuscular junction levels, we then sought to investigate whether neuregulin-1 could protect the neuromuscular junction from the damage that occurs during ageing. For this purpose, we used an in vitro co-culture model that allows the formation and maintenance of neuromuscular junctions, and we induced damage with b-amyloid incubation.

Figure 2:
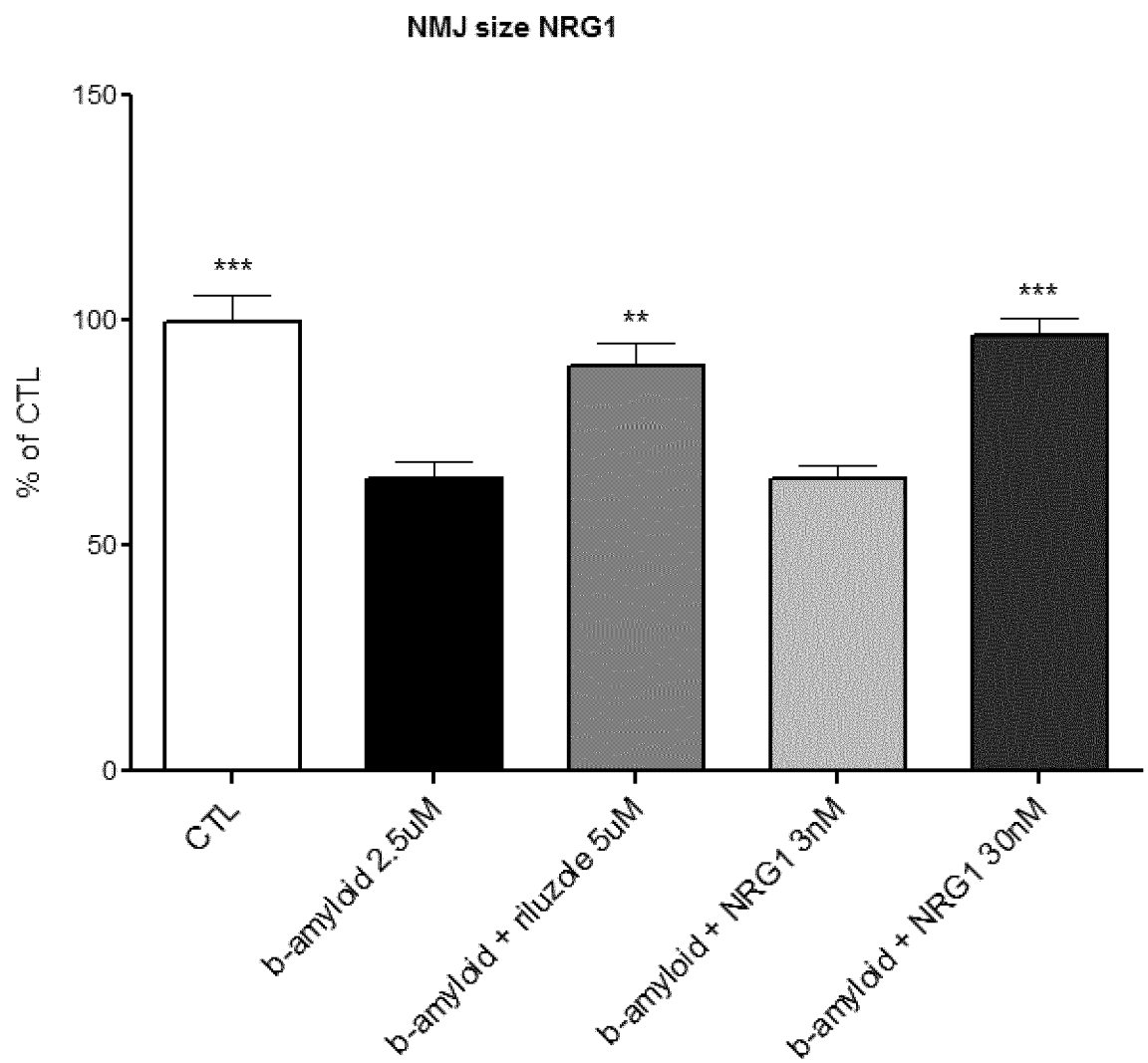

As shown in FIG. 2, neuregulin-1 was able to protect the neuromuscular system from damage at a dose of 30 nM. Collectively these results suggest that neuregulin-1 is beneficial for the maintenance of the neuromuscular system, and that the loss of this protein with age may be linked with the progression of sarcopenia.

To test whether a neuregulin-1 treatment could rescue the sarcopenia phenotype, we treated pre-sarcopenic rats for 5 months with neuregulin-1 and evaluated their skeletal muscle mass as compared with adult rats and pre-sarcopenic rats treated with saline as control.

Figure 3:
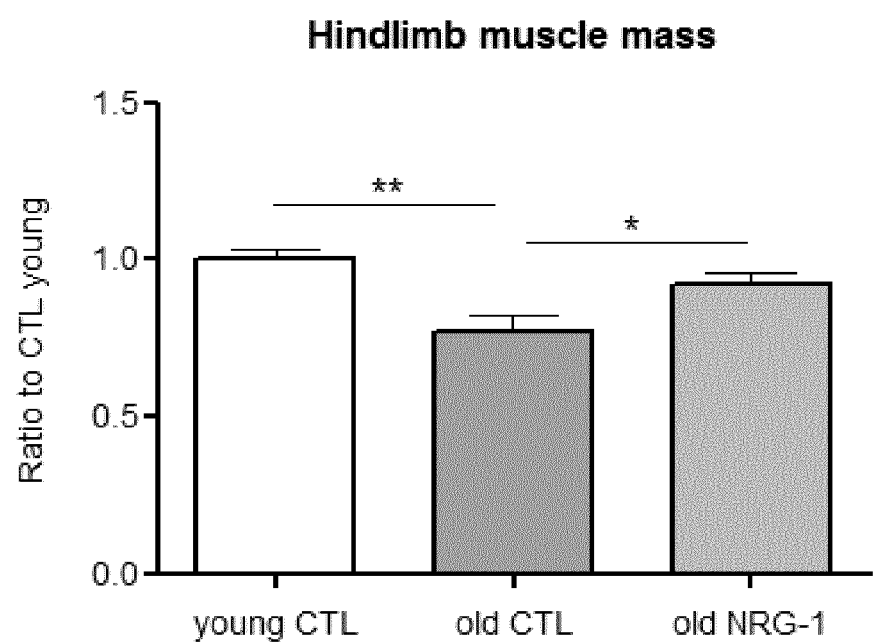

As shown in FIG. 3, we observed that hindlimb muscles from rats treated with neuregulin-1 have a significantly higher mass compared to controls, demonstrating that neuregulin-1 has prevented the age-induced skeletal muscle atrophy.

Taken together, our results suggest that neuregulin-1 protects the neuromuscular system from age-related dysfunction and could therefore be used to prevent sarcopenia.

Given the previously reported actions of vitamin B12 on neurons and the nervous system, we also tested the effect of the 2 active forms of vitamin B12 (methylcobalamin and adenosylcobalamin). Adenosylcobalamin, but not methylcobalamin, was also able to protect the system at both doses tested (FIG. 4).

Interestingly when the system was subjected to a stronger damage (longer incubation of beta-amyloid at a higher concentration), neither neuregulin-1 nor adenosylcobalamin alone could rescue the system but a co-treatment provided a mild protection suggesting that the two may have synergic effects (FIG. 5).

As shown in FIG. 6, adenosylcobalamin, but not methylcobalamin, was also able to induce an increase in muscle fiber size in aged rats.

Figure 7:
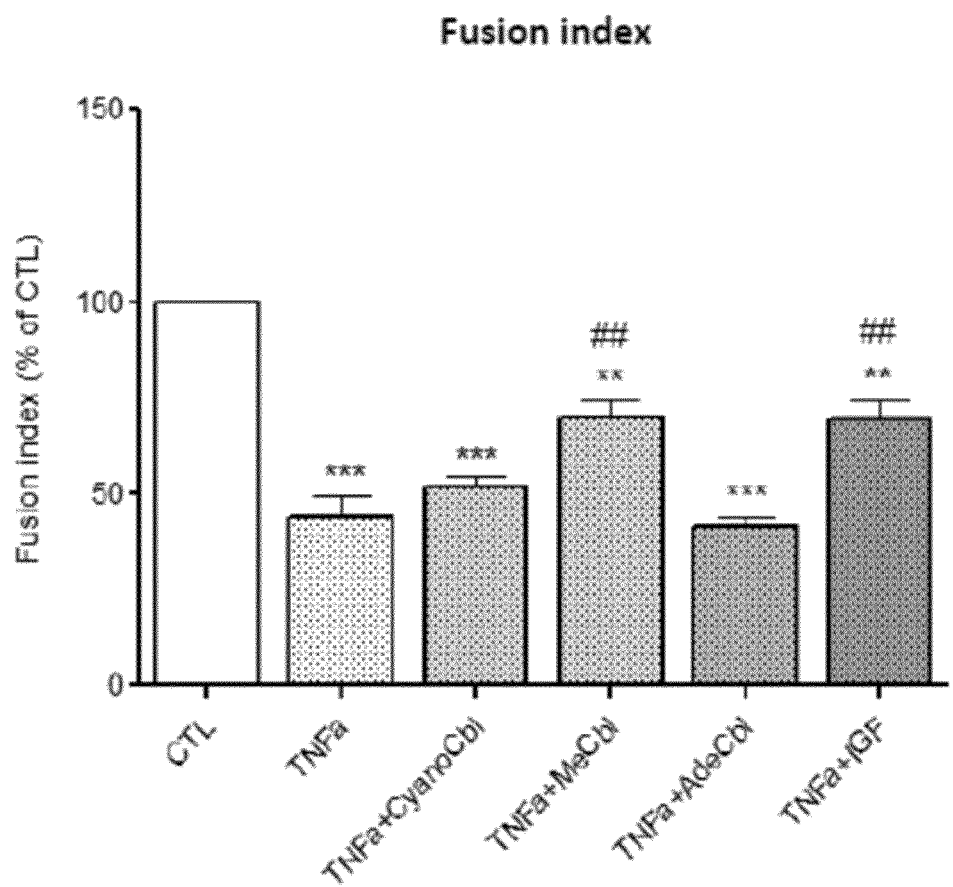

In contrast, methylcobalamin was able to protect from muscle atrophy (FIG. 7).

This differential effect may be caused by the fact that adenosylcobalamin and methylcobalamin rescue different age-related gene expression signatures in skeletal muscle (FIG. 8).

All publications mentioned in the above specification are herein incorporated by reference. Various modifications and variations of the described compounds, compositions, uses and methods of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention, which are obvious to those skilled in biochemistry and biotechnology or related fields, are intended to be within the scope of the following claims.

The invention claimed is:

1. A method of maintaining or increasing muscle function and/or mass in an ageing subject over thirty years old, the method comprising administering neuregulin-1 (NRG1) comprising the amino acid sequence of SEQ. ID. NO. 6 to the ageing subject.

2. The method of claim 1, wherein the method further comprises administering vitamin B12 to the ageing subject in need thereof.

3. The method of claim 2, wherein the vitamin B12 comprises at least one of adenosylcobalamin or methylcobalamin.

4. A method of treating sarcopenia or frailty, the method comprising administering neuregulin-1 (NRG1) comprising the amino acid sequence of SEQ. ID. NO. 6 to a subject in need thereof.

5. The method of claim 4, wherein the method further comprises administering vitamin B12 to the subject in need thereof.

6. The method of claim 5, wherein the vitamin B12 is at least one of adenosylcobalamin or methylcobalamin.

* * * * *